(12) United States Patent
Kahne et al.

(10) Patent No.: US 6,518,243 B1
(45) Date of Patent: Feb. 11, 2003

(54) DESLEUCYL GLYCOPEPTIDE ANTIBIOTICS AND METHODS OF MAKING SAME

(75) Inventors: Daniel Kahne, Princeton, NJ (US); Suzanne Walker, Princeton, NJ (US)

(73) Assignee: Trustees of Princeton University, Princeton ( * ) Notice: Subject to any disclaimer, the term of this patent is extended or adjusted under 35 U.S.C. 154(b) by 0 days.

(21) Appl. No.: 09/540,761

(22) Filed: Mar. 31, 2000

Related U.S. Application Data
(60) Provisional application No. 60/127,516, filed on Apr. 2, 1999.

(51) Int. Cl.[7] .......................... A61K 38/14; C07K 1/12; C07K 9/00
(52) U.S. Cl. ..................... 514/8; 530/322; 530/343
(58) Field of Search .................. 436/89, 90; 514/7, 514/8, 9, 11, 16, 17; 530/322, 343, 345

(56) References Cited

U.S. PATENT DOCUMENTS

| | | | |
|---|---|---|---|
| 4,643,987 A | 2/1987 | Nagarajan et al. | 514/8 |
| 4,791,100 A | 12/1988 | Kramer et al. | 514/12 |
| 5,977,063 A | 11/1999 | Thompson et al. | 514/8 |
| 6,444,786 B1 * | 9/2002 | Judice et al. | 530/317 |

FOREIGN PATENT DOCUMENTS

| | | |
|---|---|---|
| WO | WO97/02288 | 1/1997 |
| WO | WO99/56760 | 11/1999 |
| WO | 00/04044 * | 1/2000 |

OTHER PUBLICATIONS

U.S. Patent Application 09/574,225, filed May 19, 2000.*

* cited by examiner

*Primary Examiner*—Jeffrey E. Russel
(74) *Attorney, Agent, or Firm*—Kenyon & Kenyon

(57) ABSTRACT

Compounds that are analogs of glycopeptide antibiotics are disclosed. The compounds have the formula $A_1-A_2-A_3-A_4-A_5-A_6-A_7$ wherein each of the groups $A_2$ to $A_7$ is a modified or unmodified α-amino acid residue, $A_1$ is optional and, when present, is an organic group other than N-substituted leucine, and at least one of the groups $A_1$ to $A_7$ is linked via a glycosidic bond to one or more glycosidic groups each having one or more sugar residues, wherein at least one of said sugar residues is modified to bear at least one hydrophobic substituent. Methods of making these compounds, compositions including these compounds, and methods of using the compounds to treat infections in a host are also disclosed.

40 Claims, No Drawings

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial sequence
<220> FEATURE:
<223> OTHER INFORMATION: Synthetic Peptide sequence designed to
      provide antibiotic activity
<220> FEATURE:
<221> NAME/KEY: MISC_FEATURE
<222> LOCATION: (5)..(10)
<223> OTHER INFORMATION: Synthetic peptide, wherein  Xaa in positions
      from 5-10 is modified or unmodified alpha-amino acid residue.
      At least one of the residues is  linked via glycosidic bond
      to one or more glycosidic group

<400> SEQUENCE: 1

Gly Gly Gly Gly Xaa Xaa Xaa Xaa Xaa Xaa
1               5                   10
```

DESLEUCYL GLYCOPEPTIDE ANTIBIOTICS AND METHODS OF MAKING SAME

This application claims the benefit of provisional application Serial No. 60/127,516 filed Apr. 2, 1999.

BACKGROUND OF THE INVENTION

1. Field of the Invention

The present invention relates to glycopeptide compounds having antibiotic activity, and methods of making glycopeptide compounds having antibiotic activity.

2. Background of the Invention

Glycopeptide antibiotics are characterized by having at least one saccharide group chemically bonded to a rigid peptide structure having a cavity or cleft which acts as a binding site for the substrate used in bacterial cell wall synthesis. The glycopeptide antibiotics are further categorized into various subclasses depending on the identity and interconnections of the amino acids comprising the peptide backbone and the number and substitution pattern of the sugar residues in the molecule. The glycopeptide antibiotics are generally active against Gram-positive bacteria but relatively ineffective against Gram-negative bacteria. Most notable among the glycopeptide antibiotics is vancomycin. Vancomycin is produced by *Amycolatopsis orientalis,* and is often referred to as "the drug of last resort" because it is effective against most multi-drug-resistant gram positive bacteria. However, in recent years, vancomycin-resistant strains of some bacteria have emerged.

The structural formula of vancomycin is shown below and is characterized by a disaccharide moiety covalently linked to a heptapeptide structure. The structure of vancomycin places it in a class of molecules referred to as the "dalbaheptides." [Malabarba A., et al. (1997a)]. Dalbaheptides in general are characterized by the presence of seven amino acids linked together by peptide bonds and held in a rigid conformation by cross-links through the aromatic substituent groups of at least five of the amino acid residues. In the heptapeptide structure of vancomycin, which is commonly referred to as the "aglycone" of vancomycin, the aromatic side-chains of amino acids 2, 4, and 6 are fused together through ether linkages. The aromatic side-chains of amino acids 5 and 7 are joined via a carbon-carbon bond. Amino acids 1 and 3 are N-methyl leucine and asparagine, respectively. Other naturally-occurring glycopeptide antibiotics are similar to vancomycin in that they have the same amino acids 1 through 7 forming the peptide binding pocket and a glucose residue linked to the aromatic substituent on amino acid 4 through formation of a bond with a phenolic hydroxyl group. The glucose residue, in turn, is linked through its vicinal hydroxyl position to a unique amino sugar, L-vancosamine. Some glycopeptide antibiotics similar to vancomycin contain additional glycosidic groups attached to other positions on the peptide (e.g. chloroeremomycin). Still other glycopeptide antibiotics such as β-avoparcin are similar to vancomycin in that they contain the same amino acids at all positions except positions one and three. β-avoparcin, for example, contains an amino acid containing an aromatic side chain in place of the asparagine at position three and does not contain N-methyl leucine at position one. β-avoparcin contains glycosidic groups at amino acid 4 and at other positions on the peptide core.

Vancomycin, chloroeremomycin and β-avoparcin have the structures as shown below:

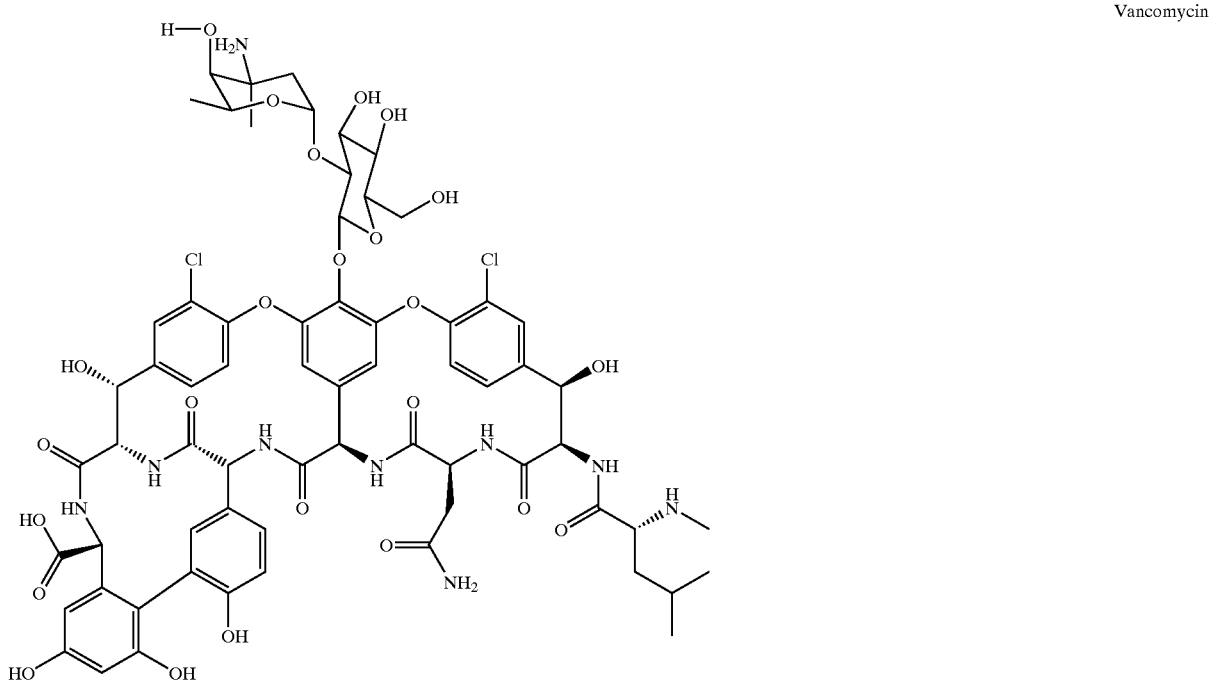

Vancomycin

-continued

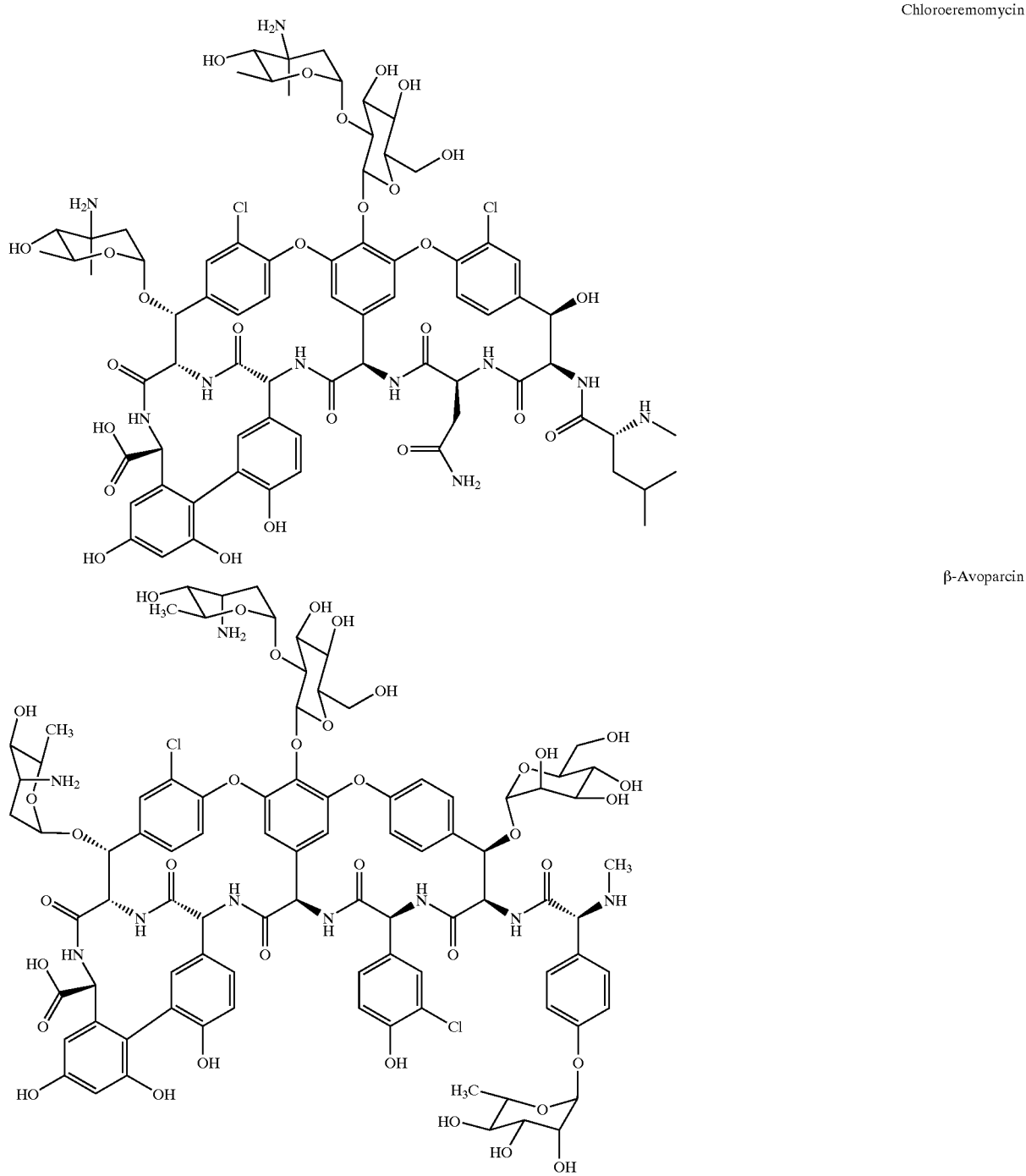

Eremomycin has the structure of chloroeremomycin except that the chlorine substituent on the aromatic group attached to amino acid 6 is not present in eremomycin.

The anti-microbial activity of the naturally occurring glycopeptide antibiotics is believed to be due to their ability to interfere with biosynthesis of the bacterial cell wall, evidently by binding to dipeptide termini of uncross-linked peptidoglycan and/or the disaccharide precursor of peptidoglycan. [Nagarajan R. (1993)]. NMR evidence has shown that the heptapeptide chain of vancomycin forms a number of hydrogen bonds with D-alanyl-D-alanine, the dipeptide that is at the terminus of the peptide chain attached to the N-acetylmuramic acid unit that is incorporated into peptidoglycan. [See, e.g., Prowse W., et al. (1995); Pierce C., et al. (1995); Williams D. et al. (1998)]. The interaction of vancomycin with peptidoglycan precursors apparently inhibits or prevents the subsequent transglycosylation and/or transpeptidation steps of cell wall assembly. Supporting this mode of action is the fact that vancomycin-resistant strains of bacteria are found to produce a pentapeptide precursor terminating in a D-alanyl-D-lactate sequence. It is hypothesized that the reduced effectiveness of vancomycin against resistant strains is due to reduced hydrogen bonding interactions between the drug and the D-alanyl-D-lactate substrate (and possibly repulsive interactions as well). The affinity of vancomycin for D-alanyl-D-lactate is estimated to be 2–3 orders of magnitude (4.1 kcal/mol) less than for D-alanyl-D-alanine. [Walsh C (1993)].

The sugar residues of vancomycin and other glycopeptide antibiotics have been shown to affect biological activities. Structural changes in the sugar residues can produce significant changes in antibiotic activity. [Malabarba (1997); Nagarajan, R. (1993)]. It has been proposed that the sugar residues on the glycopeptide antibiotics may enhance the avidity of these molecules for surface-bound peptide ligands. At least two different mechanisms for enhancing avidity have been proposed. [Kannan (1998); Gerhard (1993); Allen (1997)].

For example, it has been proposed that the biological activity of vancomycin, along with that of many other glycopeptide antibiotics, is enhanced by dimerization [Williams D., et al. (1993); Gerhard U., et al., (1993)] facilitated by the saccharide groups on the convex surface of the molecules. Structural evidence for dimerization of several different glycopeptides has been obtained from both NMR and crystallographic studies. It has been found that there are significant differences in the stability of the dimers formed in solution by different glycopeptide antibiotics. [MacKay (1994)]. Dimerization is thought to influence activity by increasing the avidity of the glycopeptides for surface-bound D-ala-D-ala peptide ligands [Williams, (1998)]. It is proposed that the differences in the dimerization constants, due to different interactions between saccharide groups, may account at least partially for the differences in biological activity of different glycopeptide antibiotics which otherwise have very similar peptide binding pockets and also have similar affinities for the natural D-ala-D-ala substrate. [Williams (1998)].

A second mechanism for enhancing activity has been proposed for the naturally occurring glycopeptide antibiotic teicoplanin and various semi-synthetic glycopeptides containing hydrophobic substituents on at least one of the saccharide units. It is suggested that hydrophobic substituents (a C2 N-acyl group in the case of teicoplanin) interact with the bacterial membrane, thus "anchoring" hydrophobically substituted glycopeptides at the membrane surface. [Beauregard (1995)]. Membrane anchoring is proposed to enhance activity by localizing the glycopeptide antibiotic to the membrane where the Lipid II substrates that are the precursors of peptidoglycan are found. The glycopeptide antibiotics then bind to the dipeptide termini of these precursors and prevent transglycosylation and/or transpeptidation.

It should be noted that teicoplanin is active against some vancomycin resistant strains. Furthermore, the attachment of hydrophobic substituents to the vancomycin carbohydrate moiety confers activity against these and other vancomycin-resistant bacterial strains. [Nagarajan (1991)]. It has been speculated that the lipophilic groups on the saccharides, in locating the antibiotic at the cell surface, help overcome the decreased binding affinity for D-ala-D-lac in vancomycin resistant microorganisms.

It has generally been assumed that peptide binding is essential for biological activity. In fact, it had been shown that if the peptide core of vancomycin is damaged by removing the N-methyl leucine (amino acid 1), the resulting compound loses affinity for D-ala-D-ala and has no biological activity, even against sensitive bacterial strains. The lack of biological activity is presumed to be due to the inability of the compound to bind D-Ala-D-Ala well.

Previously, others have explored the possibility of attaching amino acids other than N-methyl leucine to the amino acid 2 on des-N-methyl leucyl vancomycin. It was found that some amino acid substitutions produced compounds with comparable activity to vancomycin; some had worse activity. No useful improvements in activity have been reported. As far as we know, no substitutions have ever been made at the $A_1$ position of any dalbaheptides wherein $A_1$ and $A_3$ are not directly linked by a covalent bond and wherein there is at least one hydrophobic substituent on at least one of the sugar moieties attached to at least one of the amino acids $A_2$–$A_7$. Thus, replacing N-methyl leucine at $A_1$ on vancomycin with other amino acids did not yield any compounds having significantly better properties than vancomycin itself. Hence, it would not be expected that glycopeptides having at least one hydrophobic substituent attached to a glycosidic group on any one of amino acids A2–$A_7$ and having no $A_1$ group or an $A_1$ group other than an N-substituted leucine would have any antibiotic properties, much less better antibiotic properties than the precursor glycopeptide compounds.

Definitions

A "glycoconjugate" comprises any molecule linked to at least one carbohydrate of any size. The molecule can be a peptide or protein, a nucleic acid, a small molecule, a lipid, or another carbohydrate; it may be of natural or non-natural origin.

A "glycopeptide" is a glycoconjugate comprising a peptide linked to at least one carbohydrate.

A "glycopeptide antibiotic" is a glycopeptide having antibacterial activity, including, e.g., vancomycin, eremomycin, chloroeremomycin and β-avoparcin as well as any synthetic and semi-synthetic derivatives thereof. The term "glycopeptide antibiotic" is meant to encompass any naturally occurring antibiotic as well semi-synthetic derivatives thereof.

An "aglycone" is the result of removing the carbohydrate residues from a glycopeptide, leaving only a peptide core.

A "des-N-methyl leucyl aglycone" is the result of removing a terminal N-methyl leucine residue from an aglycone.

A "pseudoaglycone" is the result of removing only one of two sugar residues from a disaccharide residue linked to amino acid residue $A_4$ of a glycopeptide. Thus, a pseudoaglycone comprises an aglycone in which $A_4$ is linked to a monosaccharide residue.

A "des-N-methyl leucyl pseudoaglycone" is the result of removing a terminal N-methyl leucine residue from an pseudoaglycone. Thus, a des-N-methyl-leucyl pseudoaglycone is an aglycone in which $A_4$ is linked to a monosaccharide residue and which has a terminal N-methyl leucine residue removed therefrom.

A "dalbaheptide" is a glycopeptide containing a heptapeptide moiety which is held in a rigid conformation by cross-links between the aromatic substituent groups of at least five of the seven α-amino acid residues, including a cross-link comprising a direct carbon-carbon bond between the aryl substituents of amino acid residues 5 and 7, and aryl ether cross-links between the substituents of amino acid residues 2 and 4, and 4 and 6. Amino acid residues 2 and 4–7 in different dalbaheptides are those found in the naturally occurring glycopeptide antibiotics. These amino acid residues differ only in that residues 2 and 6 do not always have a chlorine substituent on their aromatic rings, and in that substitution on free hydroxyl or amino groups may be present. Amino acids residues 1 and 3 may differ substantially in different dalbaheptides; if both bear aryl substituents, these may be cross-linked. Molecules having a dalbaheptide structure include, e.g., the glycopeptide antibiotics mentioned above.

The term "alkyl" refers to a linear or branched acyclic or non-aromatic cyclic group having form one to twenty carbon atoms connected by single or multiple bonds. Thus, the term "alkyl" is meant to encompass linear or branched acyclic or non-aromatic groups having one or more carbon-carbon double or triple bonds, i.e., alkenyl and alkynyl groups. An alkyl group may be substituted by one or more of halo, hydroxyl, protected hydroxyl, amino, protected amino, nitro, cyano, alkoxy, aryloxy, aralkyloxy, COOH, aroyloxy, alkylamino, dialkylamino, trialkylammonium, alkylthio, arylthio, alkanoyl, alkanoyloxy, alkanoylamido, alkylsulfonyl, arylsulfonyl, aroyl, aralkanoyl, heterocyclic, $CONH_2$, CONH-alkyl, $CON(alkyl)_2$, COO-aralkyl, COO-aryl or COO-alkyl.

The term "aryl" refers to a group derived from a non-heterocyclic aromatic compound having from six to twenty carbon atoms and from one to four rings which may be fused or connected by single bonds. An aryl group may be substituted by one or more of alkyl, aralkyl, heterocyclic, heterocyclic-alkyl, heterocyclic-carbonyl, halo, hydroxyl, protected hydroxyl, amino, protected amino, hydrazino, alkylhydrazino, nitro, cyano, alkoxy, aryloxy, aralkyloxy, aroyloxy, alkylamino, dialkylamino, trialkylammonium, alkylthio, arylthio, alkanoyl, alkanoyloxy, alkanoylamido, alkylsulfonyl, arylsulfonyl, aroyl, aralkanoyl, COO-alkyl, COO-aralkyl, COO-aryl, $CONH_2$, CONH-alkyl or $CON(alkyl)_2$.

The term "aralkyl" refers to an alkyl group substituted by an aryl group. Aralkyl may optionally be substituted with one or more of the groups with which alkyl or aryl may be substituted.

The term "heterocyclic" refers to a group derived from a heterocyclic compound having from one to four rings, which may be fused or connected by single bonds; said compound having from three to twenty ring atoms which may be carbon, nitrogen, oxygen, sulfur or phosphorus. A heterocyclic group may be substituted by one or more alkyl, aryl, aralkyl, halo, hydroxyl, protected hydroxyl, amino, hydrazino, alkylhydrazino, arylhydrazino, nitro, cyano, alkoxy, aryloxy, aralkyloxy, aroyloxy, alkylamino, dialkylamino, trialkylamino, alkylthio, arylthio, alkanoyl, alkanoyloxy, alkanoylamido, alkylsulfonyl, arylsulfonyl, aroyl, aralkanoyl, COO-alkyl, COO-aralkyl, COO-aryl, $CONH_2$, CONH-alkyl or $CON(alkyl)_2$.

The terms "alkoxy," "aryloxy," and "aralkyloxy," refer to groups derived from bonding an oxygen atom to an alkyl, aryl or aralkyl group, respectively. Any alkoxy, aryloxy or aralkyloxy group may optionally be substituted with one or more of the groups with which alkyl, aryl or aralkyl may be substituted. The terms "alkanoyl," "aroyl," and "aralkanoyl" refer to groups derived from bonding a carbonyl to an alkyl, aryl or aralkyl group, respectively. Any alkanoyl, aroyl or aralkanoyl group may optionally be substituted with one or more of the groups with which alkyl, aryl or aralkyl may be substituted. The terms "heterocyclic-alkyl" and "heterocyclic-carbonyl" refer to groups derived from bonding a heterocyclic group to an alkyl or a carbonyl group, respectively. An heterocyclic-alkyl or heterocyclic-carbonyl group may optionally be substituted with one or more of the groups with which heterocyclic or alkyl may be substituted. The term "heterocyclic-alkyl-carbonyl" refers to a group derived from bonding a heterocyclic-alkyl group to a carbonyl group. Any heterocyclic-alkyl-carbonyl may optionally be substituted with one or more of the groups with which heterocyclic or alkyl may be substituted. The term "alkylsulfonyl" refers to a group derived from bonding an alkyl group to a sulfonyl group. An alkylsulfonyl group may optionally be substituted with one or more groups with which alkyl may be substituted. The term "arylsulfonyl" refers to a group derived from bonding an aryl group to a sulfonyl group. An arylsulfonyl group may optionally be substituted with one or more groups with which aryl may be substituted. The term "protected hydroxyl" refers to a hydroxyl group bonded to a group which is easily removed to generate the free hydroxyl group by treatment with acid or base, by reduction or by exposure to light, or by any other conventional means for removing a protecting group from a hydroxyl group. The term "protected amino" refers to an amino group bonded to a group which is easily removed to generate the free amino group by treatment with acid or base, by reduction or exposure to light, or by any other conventional means for removing a protecting group from an amino group.

A "chemical library" is a synthesized set of compounds having different structures. The chemical library may be screened for biological activity to identify individual active compounds of interest.

The term "DMF" refers to N,N-dimethylformamide; "THF" refers to tetrahydrofuran; "TFA" refers to trifluoroacetic acid; "EtOAc" refers to ethyl acetate; "MeOH" refers to methanol, "MeCN" refers to acetonitrile; "Tf" refers to the trifluoroacetyl group; "DMSO" refers to dimethyl sulfoxide; "DIEA" refers to diisopropylethylamine; "All" in structural formulas refers to the allyl group; "Fmoc" refers to 9-fluorenylmethyloxycarbonyl; "HOBt" refers to 1-hydroxybenzotriazole and "Obt" to the 1-oxybenzotriazolyl group; "PyBOP" refers to benzotriazol-1-yl-oxyatripyrrolidine-phosphonium hexafluorophosphate; "Su" refers to the succinimidyl group; "HBTU" refers to O-benzoatriazol-1-yl-N2N3N',N'-tetramethyfuronium hexafluorophosphate; "alloc" refers to allyloxycarbonyl; and "CBZ" refers to benzyloxycarbonyloxy.

The term "hydrophobic" as used herein to describe a compound of the present invention or a substituent thereon, refers to the tendency of the compound or substituent thereon to lack an affinity for, to repel or to fail to absorb water, or to be immiscible in water. The term "hydrophobic" is not meant to exclude compounds or substituents thereon that are not completely immiscible in water.

The term "polar" as used herein to describe a compound of the present invention or a substituent thereon, refers to the tendency of the compound or substituent thereon to have an affinity for, to attract or to absorb water, or to be miscible in water. The term "polar" is not meant to exclude compounds or substituents thereon that are not completely miscible in water.

SUMMARY OF THE INVENTION

Thus, the present invention is directed to compounds of the formula $A_1$-$A_2$-$A_3$-$A_4$-$A_5$-$A_6$-$A_7$ wherein each of the groups $A_2$ to $A_7$ comprises a modified or unmodified α-amino acid residue, $A_1$ is optional and, when present, comprises an organic group other than N-substituted leucine, and at least one of the groups $A_2$ to $A_7$ is linked via a glycosidic bond to one or more glycosidic groups each having one or more sugar residues, wherein at least one of said sugar residues is modified to bear at least one hydrophobic substituent. In preferred compounds of the present invention, the glycosidic group is a disaccharide modified to bear at least one hydrophobic substituent. In a preferred embodiment of the present invention, each of the groups $A_2$, $A_4$, $A_5$, $A_6$ and $A_7$ bears an aromatic side chain and the aromatic side chains of groups $A_2$ and $A_6$ are linked to the aromatic side chain of group $A_4$ via ether linkages and the aromatic side chains of groups $A_5$ and $A_7$ are linked to each other via a carbon-carbon bond. In another preferred embodiment of the invention, the group $A_4$ bears a glycosidic group. The glycosidic group is preferably is a disaccharide comprising a glucose residue directly bonded to group $A_4$ and a vancosamine residue bonded to said glucose residue. In preferred compounds of the present invention, $A_2$-$A_3$-$A_4$-$A_5$-$A_6$-$A_7$ is as found in a compound selected from the group consisting of vancomycin, eremomycin, chloroeremomycin, and β-avoparcin, more preferably $A_2$-$A_3$-$A_4$-$A_5$-$A_6$-$A_7$ is as found in vancomycin. In other preferred compounds of the present invention, the $C_6$ position of the glucose residue attached to $A_4$ is modified to bear at least one substituent other than hydroxyl, and more preferably the at least one substituent other than hydroxyl is a polar substituent or a hydrophobic substituent. In preferred compounds of the present invention where $A_2$-$A_3$-$A_4$-$A_5$-$A_6$-$A_7$ is as found in vancomycin, the vancosamine residue in vancomycin is N-substituted with said at least one hydrophobic substituent. In other preferred compounds of the present invention wherein $A_2$-$A_3$-$A_4$-$A_5$-$A_6$-$A_7$ is as found in vancomycin, the glucose residue attached to $A_4$ of vancomycin is modified at the $C_6$ position to bear at least one substituent other than hydroxyl, preferably a polar substituent, and said vancosamine residue is N-substituted with said at least one hydrophobic substituent. The at least one hydrophobic substituent is preferably selected from R, OR, $NR_1R$, SR, $SO_2R$, C(O)OR, C(O)SR, C(S)OR, C(S)SR, $NR_1C(O)R$, $C(O)NR_1R$, or halo and R is alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl; $R_1$ is hydrogen, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl; and any pharmaceutically acceptable salts thereof, and if two or more of said substituents are present, they can be the same or different. The organic group $A_1$ in the preferred compounds of the present invention, is preferably an organic group selected from the group consisting of a modified or unmodified alpha amino acid residue other than N-substituted leucine, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl, arylsulfonyl, guanidinyl, carbamoyl, or xanthyl. Also, in the preferred compounds of the present invention, the $A_7$ group bears a terminal carboxyl, ester, thioester, amide, N-substituted amide, or other carboxylic acid derivative, any of which groups may be substituted with any of the substituents described herein.

In another aspect, the present invention is also directed to a method for making compounds of the formula $A_1$-$A_2$-$A_3$-$A_4$-$A_5$-$A_6$-$A_7$ wherein each of the groups $A_2$ to $A_7$ comprises a modified or unmodified α-amino acid residue, $A_1$ comprises an organic group other than N-substituted leucine, and at least one of the groups $A_1$ to $A_7$ is linked via a glycosidic bond to one or more glycosidic groups each having one or more sugar residues, wherein at least one of said sugar residues is modified to bear at least one hydrophobic substituent comprising the steps of removing the N-substituted leucine residue from the compound N-substituted-leucyl-$A_2$-$A_3$-$A_4$-$A_5$-$A_6$-$A_7$ thereby forming a compound having a free amino group at $A_2$; and attaching an organic group $A_1$ to the free amino group at $A_2$, wherein the hydrophobic substituent and the groups $A_1$-$A_7$ are as described above. Preferably, the N-substituted-leucine residue is N-methyl leucine. This method is applicable to any of the preferred compounds as described above.

In another aspect, the present invention is directed to a method for making a glycopeptide antibiotic having the formula $A_1$-$A_2$-$A_3$-$A_4$-$A_5$-$A_6$-$A_7$ wherein $A_2$-$A_3$-$A_4$-$A_5$-$A_6$-$A_7$ is as found in vancomycin and $A_1$ comprises an organic group other than N-substituted leucine, said method comprising modifying vancomycin to form a modified vancomycin bearing a hydrophobic substituent at the vancosamine nitrogen; removing the N-methyl leucine residue from the modified vancomycin to form a des-N-methyl leucyl modified vancomycin bearing a free amino group at $A_2$ and attaching an organic group $A_1$ to the amino group at $A_2$, wherein the hydrophobic substituent and the organic group $A_1$ are as defined above.

In another aspect, the present invention is directed to a method for making a glycopeptide antibiotic having the formula $A_1$-$A_2$-$A_3$-$A_4$-$A_5$-$A_6$-$A_7$ wherein $A_2$-$A_3$-$A_4$-$A_5$-$A_6$-$A_7$ is as found in vancomycin and $A_1$ comprises an organic group other than N-substituted leucine, said method comprising modifying vancomycin to form a first modified vancomycin bearing a substituent other than hydroxyl at the $C_6$ position of the glucose attached to $A_4$ of vancomycin; modifying said first modified vancomycin to form a second modified vancomycin bearing a hydrophobic substituent at the vancosamine nitrogen; removing the N-methyl leucine residue from said second modified vancomycin to form a des-N-methyl leucyl second modified vancomycin bearing a free amino group at $A_2$; and, attaching an organic group $A_1$ to the amino group at $A_2$, wherein the hydrophobic substituent and the organic group $A_1$ are as described above. It is preferred in this method that the substituent other than hydroxyl at the $C_6$ position of the glucose attached to $A_4$ of vancomycin is a polar substituent.

The present invention is also directed to a method of treating an infectious disease in a host comprising administering to said host an effective amount of a compound of the present invention, or a pharmaceutically acceptable salt or ester thereof. Preferably the host is a mammalian host, more preferably a human. The infectious disease is preferably a bacterial infection. The present invention is also directed to a composition comprising a compound of the present invention or a pharmaceutically acceptable salt or ester thereof and a pharmaceutically acceptable carrier or excipient. The compound of the present invention may be administered solely or in combination with any other drug or therapeutic agent.

The present invention is also directed to a method for removing an N-terminal amino acid residue from an oligopeptide or polypeptide comprising reacting an oligopeptide or a polypeptide with phenylisothiocyanate in a pyridine-water-triethylamine solvent medium. Preferably, the reaction of the oligopeptide or polypeptide with phenylisothiocyanate is carried out in a 10:10:1 (volume) pyridine-water-triethylamine solvent medium. The reaction is preferably carried out at a temperature in the range of from 40–70° C. and for a period of time in the range of from 20–60 minutes. In preferred methods, the N-terminal amino acid residue is N-methyl leucine. The preferred oligopeptides are selected from the group consisting of a glycopeptide antibiotic, a pseudoaglycone and an aglycone, preferably a glycopeptide antibiotic or pseudoaglycone in which at least one of the glycosidic groups therein is modified to bear at least one hydrophobic substituent. Preferably, the glycopeptide antibiotic is vancomycin. More preferably, the disaccharide at $A_4$ of vancomycin is modified to bear at least one hydrophobic group. Preferably, the vancosamine nitrogen at $A_4$ of vancomycin is modified to bear at least one hydrophobic group. In preferred methods, the glucose residue attached directly to $A_4$ of vancomycin is modified to bear at least one substituent other than hydroxyl, which is preferably a polar substituent or a hydrophobic substituent. Where the glucose residue is modified to bear at least one substituent other than hydroxyl, it is preferred that the $C_6$ position of the glucose residue attached directly to $A_4$ of vancomycin is modified to bear a polar or a hydrophobic substituent.

DETAILED DESCRIPTION OF THE INVENTION

Herein we disclose strategies for finding promising glycopeptide compounds with good activity against sensitive and resistant bacterial strains. One strategy involves attaching substituents to the free amino group of amino acid 2 in des-N-substituted-leucine glycopeptides and analogs thereof containing at least one hydrophobic substituent on a glycosidic group attached to one of the amino acids $A_2$–$A_7$. We have also discovered that where at least one of the glycosidic groups attached to one of the amino acids $A_2$–$A_7$ bears a hydrophobic substituent, it is not necessary to attach a group to the free amino group of amino acid $A_2$ upon removal of the N-substituted leucine residue in order to produce compounds having biological activity. Thus, we have found good activity in des-N-substituted leucine glycopeptide compounds in which at least one of the glycosidic groups attached to one of the amino acids $A_2$–$A_7$ bears a hydrophobic substituent and in which $A_2$ bears a free amino group upon removal of the N-substituted leucine residue therefrom. We have demonstrated the utility of the strategy by making a set of compounds, of which several have better activity against a range of strains than the corresponding compounds in which $A_1$ is N-substituted leucine, which is preferably N-methyl leucine. Some of the substitutions improve activity against both sensitive and resistant strains relative to N-methyl leucine; others improve activity more against sensitive strains than resistant strains; still other improve activity more against resistant strains than sensitive strains. Thus, it is possible to manipulate the biological activity in different ways by choosing appropriate $A_1$ substituents. It is also possible to manipulate the biological activity by choosing appropriate hydrophobic substituents. We also show that the physical properties of the compounds—e.g., the hydrophobic-hydrophilic balance as measured by HPLC retention times—are related to both the hydrophobic substituent, and when present, the specific group $A_1$. Having shown that both the physical properties and the biological activities of glycopeptide derivatives containing hydrophobic substituents on the sugars are affected by the identity of the hydrophobic substituent and, when present, the group $A_1$, the present invention is thus directed to all compounds of the general structure $A_1$-$A_2$-$A_3$-$A_4$-$A_5$-$A_6$-$A_7$ wherein the group $A_1$ is optional and, when present, is preferably an organic group having from 2–30 carbon atoms, which may contain heteroatoms. The organic group $A_1$ may contain more than 30 carbon atoms. The organic group $A_1$, when present, is attached to the amino group at $A_2$. The organic group $A_1$ may be linear, branched or cyclic, or some combination thereof, and may include aliphatic, aromatic, and/or heterocyclic groups, provided that it is not a leucine or a modified leucine residue, and provided that it is not directly or indirectly linked by a covalent bond to amino acid 3. Preferably the organic group is a modified or unmodified alpha amino acid residue, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl, arylsulfonyl, guanidinyl, carbamoyl, or xanthyl.

When present, preferred AI groups are provided by the compounds listed in Table I following Example 3. The structural formulae of these preferred $A_1$ groups are also provided in Table I. These are merely preferred $A_1$ groups, and the present invention is not to be construed as being limited thereto. In general, $A_1$ can be any organic group that can be reacted with the free amino group at $A_2$ by, for example, formation of an amide linkage. Thus, preferred reagents which can be reacted with the free amino group at $A_2$ include compounds having a carboxylic acid group which reacts with the free amino group at $A_2$ to form the amide linkage. Such preferred compounds include those disclosed in Table I.

In preferred compounds of the present invention, each of the groups $A_2$ to $A_7$ comprises a modified of unmodified α-amino acid residue, whereby (i) the group $A_1$, when present, is linked to an amino group on the group $A_2$, (ii) each of the groups $A_2$, $A_4$ and $A_6$ bears an aromatic side chain, which aromatic side chains are cross-linked together by two or more covalent bonds, and (iii) the group $A_7$ bears a terminal carboxyl, ester, thioester, amide, N-substituted amide, or other derivative of a carboxylic acid.

In the compounds of the present invention, one or more of the groups $A_2$ to $A_7$ is linked via a glycosidic bond to one or more sugar resides; wherein at least one of said sugar resides bears at least one hydrophobic substituent wherein the hydrophobic substituent is preferably selected from R, OR, $NR_1R$, SR, $SO_2R$, C(O)OR, C(O)SR, C(S)OR, C(S)SR, $NR_1C(O)R$, $C(O)NR_1R$, or halo and R is alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl; $R_1$ is hydrogen, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl; and any pharmaceutically acceptable salts thereof, and if two or more of said substituents are present, they can be the same or different.

Modified amino acid residues include amino acid residues whose aromatic groups have been substituted by halo, alkyl, alkoxy, alkanoyl, or other groups easily introduced by electrophilic substitution reactions or by reaction of phenolic hydroxyl groups with alkylating or acylating agents; and amino acid residues which have protecting groups or other easily introduced substituents on their hydroxyl or amino groups including, but not limited to alkyl, alkanoyl, aroyl, aralkyl, aralkanoyl, carbamoyl, allyloxycarbonyl, aralkyloxycarbonyl, aryloxycarbonyl, alkylsulfonyl, arylsulfonyl, heterocyclic, heterocyclic-alkyl or heterocyclic-carbonyl substituents. Examples of preferred protecting groups include acetyl, allyloxycarbonyl (aloc), CBZ, allyl, benzyl, p-methoxybenzyl and methyl. Modifications of hydroxyl groups occur on phenolic hydroxyl groups, benzylic hydroxyl groups, or aliphatic hydroxyl groups. Other amino acid residues, in addition to $A_2$, $A_4$ and $A_6$ may be cross-linked through their aromatic acid substituent groups.

In the preferred compounds of the present invention, the residues $A_2$ to $A_7$ of the glycopeptides are linked sequentially by peptide bonds and are cross-linked as in a dalbaheptide. The preferred glycopeptides have a peptide core in which the residues are linked as in the glycopeptide antibiotics vancomycin, eremomycin, chloroeremomycin or β-avoparcin. In particularly preferred compounds of the present invention, the structures and interconnections of $A_2$ to $A_7$ are those of vancomycin, i.e., those having the heptapeptide core of vancomycin with the N-methyl leucine residue removed, subject to the amino acid modifications and substitutions described herein above.

The glycopeptide compounds of the present invention contain at least one glycosidic group attached through a glycosidic bond to at least one of the amino acid residues $A_2$ to $A_7$. In the preferred compounds of the present invention, a glycosidic group is linked to residue $A_4$. This glycosidic group comprises at least a monosaccharide bearing at least one hydrophobic substituent. Preferably, the glycosidic group is a disaccharide residue bearing at least one hydrophobic substituent which disaccharide residue can be linked to any of the amino acid residues $A_2$–$A_7$, preferably to the amino acid residue $A_4$. In the particularly preferred compounds of the present invention, the glycosidic group attached to $A_4$ is a disaccharide consisting of a glucose residue directly attached to the amino acid $A_4$ and an N-substituted vancosamine residue attached to the glucose residue. Preferably, the vancosamine residue is N-substituted with the at least one hydrophobic substituent. Examples of preferred hydrophobic substituents which are preferably present as N-substituents on the vancosamine residues are shown below:

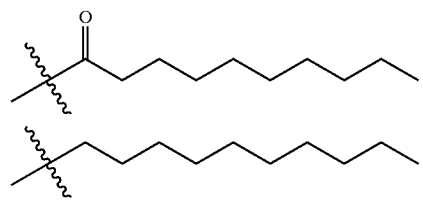

Chain lengths from $C_8$ to $C_{15}$, could also be branched alkyl, halo alkyl, halo alkoxy.

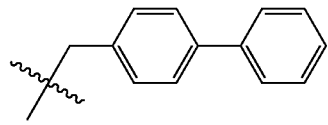

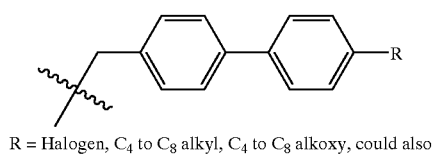

R = Halogen, $C_4$ to $C_8$ alkyl, $C_4$ to $C_8$ alkoxy, could also have more R groups (up to five)

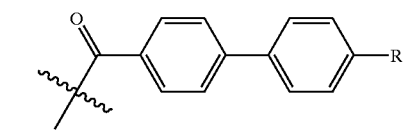

R = Halogen, $C_4$ to $C_8$ alkyl, $C_4$ to $C_8$ alkoxy, could also have more R groups (up to five)

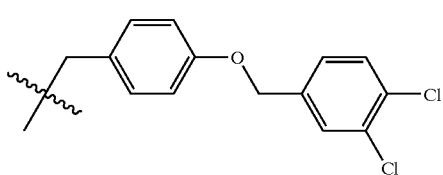

-continued

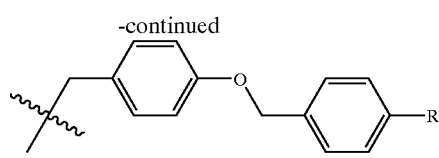

R = Halogen, $C_4$ to $C_8$ alkyl, $C_4$ to $C_8$ alkoxy, could also have more R groups (up to five)

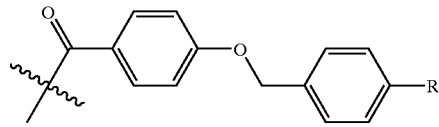

R = Halogen, $C_4$ to $C_8$ alkyl, $C_4$ to $C_8$ alkoxy, could also have more R groups (up to five)

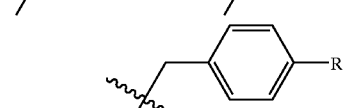

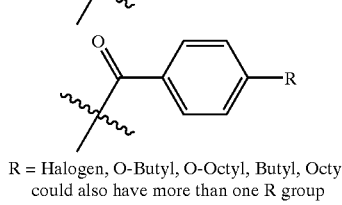

R = Halogen, O-Butyl, O-Octyl, Butyl, Octyl could also have more than one R group Thus, preferred N-substituents at the vancosamine nitrogen include, e.g., straight or branched alkyl, aralkyl, alkanoyl, aralkanoyl and aroyl. Any of these N-substituents may be substituted with one or more of alkyl, preferably $C_4$–$C_8$ alkyl, halo, haloalkyl, aryl, aralkyl, aryloxy, aralkyloxy, alkaryloxy, alkoxy, preferably $C_4$–$C_8$ alkoxy, and haloalkoxy. Preferred alkoxy substituents on the N-substituent include, e.g., O-butyl and O-octyl. Where the N-substituent is alkyl, it is preferred that alkyl has from 8 to 15 carbon atoms. Specific preferred N-subsitutents include, but are not limited to the following:
2-naphthylmethyl
4-phenylbenzyl
1-naphthylmethyl
4-phenoxybenzyl;
4-benzyloxybenzyl
4-trifluoromethoxybenzyl
4-allyloxybenzyl
4-nonyloxybenzyl;
2-methoxy-1-naphthylmethyl
4-dodecyloxybenzyl
9-phenanthranylmethyl
4-decyloxybenzyl
9-anthranylmethyl
4-[phenylethyl]4-phenylbenzyl
4-methoxy-1-naphthylmethyl
1-pyrenylmethyl
9-[10-methyl]anthranylmethyl
9-[10-chloro]anthranylmethyl
2-benzthienylmethyl
4-[4-hydroxyphenyl]benzyl
4-[4-octylphenyl]benzyl
4-[4-pentylphenyl]benzyl
4-[4-octyloxyphenyl]benzyl
3-pyridylmethyl
5-nitro-1-naphthylmethyl 4-pyridylmethyl
4-quinolylmethyl
3-quinolylmethyl
4-stilbenzyl
2-quinolylmethyl
2-pyridylmethyl
2-fluorenylmethyl
4-phenoxyphenethyl
4-[4-pentylcyclohexyl]benzyl
4-benzylphenethyl
4-[4-biphenyl]benzyl
4-trifluoromethylbenzyl
trans-cinnamyl
4-[1-oxa]fluorenylmethyl
4-[4-pentoxyphenyl]benzyl
4-thiomethylbenzyl
2,3-[2-methyl-3-[4-t-butylphenyl]]propenyl
9-(1-methyl)-acridinylmethyl
2-hydroxy-1-naphthylmethyl
4-[2-phenyl-6-methoxy]quinoylmethyl
4-diphenylmethylbenzyl
3,4 cyclohexenylmethyl
3,4-methylenedioxylbenzyl
3-phenoxybenzyl
4-benzylbenzyl
3-benzyloxy-6-methoxy benzyl
4-benzyloxy-3-methoxybenzyl
3,4-dibenzyloxybenzyl
4-[4-methoxyphenyl]benzyl
4-[3-cyanopropoxy]benzyl
3,4-ethylenedioxybenzyl
4-[4-nitrophenoxy]benzyl
2,3-methylenedioxybenzyl
2-benzyloxyphenethyl
2-ethoxy-1-naphthylmethyl
2-benzylfurylmethyl
3-phenoxyphenethyl
4-phenoxyphenethyl
4-[4-nitrophenyl]benzyl
6-methoxy-2-naphthylmethyl
3-methyl-5-thienylmethyl
5-phenyl-2-thienylmethyl
4-benzyloxyphenethyl
3-benzyloxyphenethyl
4-[2-nitrophenoxy]benzyl
5-[4-methoxyphenyl]-2-thienylinethyl
4-difluormethoxybenzyl
2,3,4,5,6-pentamethylbenzyl
5-iodo-2-thienylmethyl
4-[2-[2-chloroethoxy]ethoxy]benzyl
3,4-dimethylbenzyl
3-acetoxybenzyl
4-nitrobenzyl
4-phenylethynylbenzyl
4-[2-chloro-6-fluorobenzyloxy]benzyl
4-[3,4-dichlorophenoxy]benzyl
4-[3,4-dichlorobenzyloxy]benzyl
S-[2,3-dihydrobenzfuryl]methyl
4-[2-[N,N-diethylamino]ethoxy]benzyl
2-bicyclo[2.1.2]heptylmethyl
2-hydroxy-5-phenylbenzyl
3-[4-chlorophenoxy]benzyl
4-[3-chlorophenoxy]-3-nitrobenzyl
4-[2-chlorophenoxy]-3-nitrobenzyl
3,5-dimethylbenzyl
4-[4-ethylphenyl]benzyl
3-phenylbenzyl
4-[3-fluorophenyl]benzyl
4-[4-chlorobenzyloxy]benzyl
4-[4-chlorophenoxy]-3-nitrobenzyl
4-[4-methylphenoxy]benzyl
4-[4-t-butylphenoxy]benzyl
4-[4-methylphenyl]benzyl
4-[4-methoxyphenoxy]benzyl
4-acetoxy-3-methoxybenzyl
4-[(2-phenyl)ethyl]benzyl
3-[5-phenyl]pyridinylmethyl
4-[2-nitrophenyl]benzyl
2-[1-hydroxy]fluorenylmethyl
4-benzyl-3-methoxybenzyl
4-[cyclohexylmethoxy]-3-ethoxybenzyl
3-[3,3'-dichlorophenoxy]benzyl
4-[4-propylphenyl]benzyl
4-thiophenylbenzyl
4-[alpha-hydroxybenzyl]benzyl
2,2-dinitro-4-thiophenebenzyl
3-[3-trifluoromethylphenoxy]benzyl
4-[t-butylethynyl]benzyl
4-phenoxy-3-methoxy-benzyl
4-[3-trifluoromethylphenoxy]-3-nitrobenzyl
2-phenylthiobenzyl
2-[4-chlorophenyl]-6-benzoxazolemethyl
4-[alpha-methoxybenzyl]benzyl
4-cyclohexylbenzyl
3-[3,4-dichlorophenoxy]benzyl
acenaphthlenylmethyl
4-[1,1,2,2-tetrafluoroethoxy]benzyl
4-benzoyloxy-3,3-dimethoxybenzyl
3-[cyclohexylmethoxy]benzy)
4-cyclohexyloxybenzyl
3-[2-quinoylmethoxy]benzyl
4-[alpha-ethoxybenzyl]benzyl
4-[cyclohexylethoxy]benzyl
4-[alpha-propoxybenzyl]benzyl
4-[4-methyl-1-piperidino]benzyl
2-thiophene-1,2-cyclohexenylmethyl
4-[4-nitrobenzyloxy]benzyl
3-[4-trifluoromethylphenoxy]benzyl
3-benzoyl-2,4-dichlorobenzyl
4-[2-[2-thiopropyl]ethoxy]benzyl
4-[2-methyl-1-piperidino]benzyl
4-hydroxybenzyl
4-[2-pyridyl]benzyl
4-acetoxybenzyl
5,6-benzonorbornylmethyl
3-phenylcyclopentylmethyl
1-adamantylmethyl
3-[cyclohexylmethoxy]-4-methoxybenzyl
2-[2-glucosyl]benzyl
4-[4-pentoxybiphenyl]benzyl
3,4-dihydroxybenzyl
4-[4-methylpiperazino]benzyl
4-morpholinobenzyl
4-[4-chlorophenylsulfonyl]benzyl
4-methylsulfonyloxybenzyl
4-benzoyloxybenzyl
5-phenyl-3-pyridinylmethyl
4-[N,N-bis(2-chloroethyl)amino]benzyl
3-cyclohexyloxybenzyl
4-[2-t-butoxyethoxy]benzyl
3,3-dichloro-4-hydroxy-benzyl
1,2,3,4,-tetrahydro-9-anthranylmethyl
4-cyclohexanoyloxybenzyl
4-nonanoyloxybenzyl 4-[phenylsulfinyl]benzyl
4-anilinobenzyl
cyclohexylmethyl
3-benzoyloxybenzyl
3-nonanoyloxybenzyl
4-[cyclohexyl]cyclohexylmethyl
3-cyclohexanoyloxybenzyl
4-[cyclohexanoyloxy]-3,3-[dimethoxy]benzyl
4-[nonanoyloxy]-3,3-[dimethoxy]benzyl
1,2,3,4-tetrahydro-6-naphthylmethyl
2-hydroxybenzyl
[2-[6,6-dimethyl-bicyclo[3.1.1]hept-2-enyl]methyl
1-cyclohexenyl-4-isopropylmethyl
4-[4-methoxyphenyl]butyl
4-[[2,3,4,5,6-pentamethyl]phenylsulfonyloxy]benzyl
4-[1-pyrrolidinosulfonyl]benzyl
3-[4-methoxyphenyl]propyl
8-phenyloctyl
4-[2,3-dihydroxypropoxy]benzyl
4-[N-methylanilino]benzyl
2-[2-napthyl]ethyl
6-methyl-2-naphthylmethyl
cis-bicyclo[3.3.0]octane-2-methyl
2-tridecynyl
4-butyl-2-cyclohexylmethyl
4-[(4-fluorobenzoyl)amino]benzyl
4-[(3-fluorobenzoyl)amino]benzyl
8-phenoxyoctyl
6-phenylhexyl
10-phenyldecyl
8-bromooctyl
11-tridecynyl
8-[4-methoxyphenoxy]octyl
8-[4-phenylphenoxy]octyl
8-[4-phenoxyphenoxy]octyl
3-[3-trifluoromethylphenoxy]benzyl
10-undecenyl
4-cyclohexylbutyl
4-phenyl-2-fluorobenzyl
7-hexadecynyl
3-[cyclopentyl]propyl
4-[2-methylphenyl]benzyl
4-[phenylazo]benzyl
4-[4-flurophenyl]benzyl
3-nitro-4-[4-nitrophenyl]benzyl
3-nitro-4-[2-nitrophenyl]benzyl
9-decenyl
4-[3,4-dimethoxyphenyl]benzyl
4-[4-trifluromethylphenyl]benzyl
5-hexenyl
4-[2-thienyl]benzyl
4-[6-phenylhexyloxy]benzyl
9,10-dihydro-2-phenantrene methyl
4-[3,4-dimethylphenyl]benzyl
4-[4-methylphenyl]-2-methylbenzyl
4-[3-phenylpropyloxy]benzyl
4-[3-methylphenyl]benzyl
4-[4-methylphenyl]-3-methylbenzyl
4-[4-pentenyloxy]benzyl
4-[1-heptynyl]benzyl
3-[4-t-butyl-phenylthio]benzyl
4-[4-chlorophenyl]benzyl
4-[4-bromophenyl]benzyl
4-[4-cyanophenyl]benzyl
4-[1-nonynyl]benzyl
4-[11-tridecynyloxy]benzyl
12-phenyldodecyl
6-phenyl-5-hexynyl
11-phenyl-10-undecynyl
4-[2-methylphenyl]-3-methylbenzyl
3-[2-thienyl]-2-thienylmethyl
4-[benzyloxymethyl]cyclohexylmethyl
4-[4-chlorophenoxy]benzyl
4-[benzyl]cyclohexylmethyl
4-benzoylbenzyl
4-[phenoxymethyl]benzyl
4-[4-chlorobenzyl]benzyl In another preferred embodiment of the present invention, the glucose residue attached to $A_4$ is modified to bear a substituent, which may be any of the hydrophobic substituents as described above as well as polar substituents. Thus, the preferred compounds of the present invention encompass compounds in which the vancosamine residue is N-substituted with a hydrophobic substituent and the glucose residue is modified to bear a substituent other than hydroxyl. Preferably, it is the $C_6$ position of the glucose residue that is modified to bear a substituent other than hydroxyl as described above. Thus, in particularly preferred compounds of the present invention, the vancosamine residue is N-substituted with a hydrophobic substituent and the glucose residue is also modified at the $C_6$ position to bear a substituent other than hydroxyl. Where the vancosamine residue is N-substituted with a hydrophobic substituent and the glucose residue is also modified to bear a substituent other than hydroxyl, it is preferred that glucose residue attached to $A_4$ is substituted with a polar substituent. Examples of preferred substituents on the glucose residue, and in particular at the $C_6$ position of the glucose residue include, but are not limited to, mesitylenesulfonyl; 2-thio-6-azathymine; 2-thio-4-hydroxy-6-methylpyrimidine; 2-thio-5-amino-1,3,4-thiadiazole; 2-thio-4-amino-3-hydrazino-1,2,4-triazole; 2-thio-4-hydroxy-6-methylpyrimidine; 2-thio-6-azathymine; iodo; amino; azido; bromo; hydrazino; iminotriphenylphosphoranyl; S-3-amino-5-mercapto-1,2,4-triazolyl; N-2-quinoxalinyl-Vancosamine. It is to be understood that the $C_6$ position can also be modified to bear any of the hydrophobic substituents as described above. Thus, where the $C_6$ position of the glucose residue attached directly to $A_4$ is modified to bear a hydrophobic substituent as described above, it is not necessary that the vancosamine residue attached to the glucose residue also bear a hydrophobic substituent as well. However, it is possible that both the glucose and vancosamine glycosidic groups at the $A_4$ position can be modified to bear a hydrophobic substituent.

The invention is not intended to be limited to the embodiments described above. Thus, beneficial effects of at least some of the $A_1$ substituent replacements on a dalbaheptide in which $A_1$ is not covalently linked to $A_3$ would be expected to apply generally to glycopeptide derivatives containing at least one hydrophobic group on a sugar covalently bonded to the peptide.

The compounds of the present invention can be prepared by removing the terminal N-substituted leucine residue from a compound of the formula N-substituted leucyl-$A_2$-$A_3$-$A_4$-$A_5$-$A_6$-$A_7$ wherein at least one of the glycosidic groups attached to any of $A_2$–$A_7$ bears a hydrophobic substituent to form the compound des-N-substituted-leucyl-$A_2$-$A_3$-$A_4$-$A_5$-$A_6$-$A_7$ bearing a free amino group at $A_2$ and then attaching the group $A_1$ to the free amino group at $A_2$ to form a compound of the present invention. The N-substituted leucine residue is preferably N-methyl leucine. The terminal N-substituted leucine residue can be removed by any conventional process for removing a terminal amino acid from an oligopeptide or polypeptide. One conventional method to remove a terminal amino acid is Edman degradation. This method is described in the literature and can be readily employed to remove a terminal N-substituted leucine residue in a process of making the compounds of the present invention. As applied to the method of forming the des-N-methyl leucyl compounds of the present invention, Edman degradation involves the reaction of the amino group of the terminal N-methyl leucine residue with phenyl isothiocyanate in a suitable solvent. An intermediate thiourea compound is formed, and the N-methyl leucine residue splits off from the thiourea as a phenylthiohydantoin, resulting in the corresponding des-N-methyl leucine compound.

Thus, the N-methyl leucine residue can be removed from the compound N-methyl leucyl-$A_2$-$A_3$-$A_4$-$A_5$-$A_6$-$A_7$ by reacting this compound with phenylisothiocyanate in a suitable organic solvent, preferably a pyridine-water solvent, more preferably, a 1:1 pyridine-water solvent at a temperature of about 50° C. This reaction generates the corresponding thiourea, which is then treated with TFA-$CH_2Cl_2$ to yield the des-N-methyl leucyl compound, to which the group $A_1$ can optionally be attached as described in more detail below.

The present inventors have also discovered a modified Edman degradation procedure by which an N-terminal amino acid residue can be removed from a polypeptide or an oligopeptide. This procedure involves reacting the N-terminal amino acid residue on the polypeptide or oligopeptide with phenylisothiocyanate in a pyridine-water-triethylamine solvent medium. The pyridine-water-triethylamine solvent medium preferably comprises pyridine-water-triethylamine in a ratio of 10:10:1 by volume. The reaction is conducted for about 20 to 60 minutes, with 60 minutes preferred. While not wishing to be bound by any particular theory, it is believed that triethylamine is a key reagent in this modified Edman degradation protocol. It is believed that the triethylamine catalyzes the in situ conversion of the initially formed thiourea to the final product.

In the context of the present invention, the modified Edman degradation process described above can be applied to remove the terminal N-substituted leucine residue from the compound N-substituted leucyl-$A_2$-$A_3$-$A_4$-$A_5$-$A_6$-$A_7$ wherein at least one glycosidic group attached to any of $A_2$–$A_7$ bears a hydrophobic substituent to yield the corresponding desleucyl compound bearing a free amino group at $A_2$ which can then be reacted with the organic group $A_1$ to yield the compounds of the present invention. Thus, the compound N-substituted leucyl-$A_2$-$A_3$-$A_4$-$A_5$-$A_6$-$A_7$, wherein the N-substituted leucine residue is preferably N-methyl leucine, is reacted with phenylisothiocyanate in a pyridine-water-triethylamine solvent medium, preferably a 10:10:1 pyridine-water-triethylamine solvent medium and at a temperature of about 50° C. This method yields the corresponding des-N-methyl leucyl compound in one step in nearly quantitative yield. The desired des-N-methyl leucine compound can be precipitated from DMF by adding excess of 20% ethyl acetate-hexane. The resulting product is then suitably pure for a subsequent optional step of attaching the group $A_1$ to the free amino group at $A_2$ on the des-N-methyl leucine compound to form a compound of the present invention.

Any conventional method can be employed to attach the group $A_1$ to the free amino group at $A_2$ after removal of the terminal N-substituted leucine residue. Such methods of coupling amino groups to other organic groups are well known to the ordinarily skilled chemist. In the preferred compounds of the present invention the group $A_1$ is attached to the free amino group at $A_2$ by forming an amide linkage. Thus, a carboxylic acid or other amine-reactive compound can be reacted with the free amino group at $A_2$ to form preferred compounds of the present invention. It is also possible to attach the organic group to the free amino group at $A_2$ by reductive alkylation or other common methods of functionalizing amino groups. It may be desirable in some cases when attaching the group $A_1$ to the free amino group at $A_2$ to suitably protect free amino groups at other positions in the intermediate compound so as to selectively attach the $A_1$ group to the free amino group at $A_2$. Such methods of selectively protecting free amino groups and selectively removing the protective groups are well known to the ordinarily skilled chemist. Suitable protecting groups for free amino groups include 9-fluorenylmethyloxycarbonyl (Fmoc), benzyloxycarbonyl (CBZ), tert-butyloxycarbonyl (t-Boc), and allyloxycarbonyl (alloc).

Preferably, the terminal N-substituted leucine residue is removed from a dalbaheptide wherein at least one of the groups $A_2$–$A_7$ is linked via a glycosidic bond to one or more glycosidic groups each having one or more sugar residues and wherein at least one of the sugar residues is modified to bear at least one hydrophobic substituent as described above. Thus, for example, N-methyl leucine can be removed from the dalbaheptide vancomycin in which the vancosamine residue is N-substituted with a hydrophobic substituent and which optionally may also be substituted on the glucose residue, preferably at the $C_6$ position thereof, with either a hydrophobic or, more preferably, a polar substituent as described above. Also, N-methyl leucine can be removed from the dalbaheptide vancomycin in which the $C_6$ position is modified to bear a hydrophobic substituent and in which the vancosamine nitrogen optionally also bears a hydrophobic substituent. The modified des-N methyl leucyl vancomycin can then be reacted to attach the $A_1$ substituent to form the compounds of the present invention.

An N-substituted vancomycin glycopeptide can be prepared by attaching a hydrophobic substituent to the amino group on the vancosamine residue by reductive alkylation or other conventional methods for functionalizing an amino group. Thus for example, an aldehyde can be reacted with vancomycin in a suitable organic solvent, followed by reduction of the aldehyde carbonyl group with a suitable reducing agent followed by conventional separation and purification, which may involve recrystallization and/or reverse phase chromatographic techniques as are well known to the ordinarily skilled chemist. In some cases it may be desirable to selectively protect the amino group in the N-methyl leucine residue prior to the reductive alkylation of the vancosamine nitrogen. Any amino protecting group may be employed and conventional methods of removing the amino protecting group may be employed to remove the protective group after performing the reductive alkylation at the vancosamine nitrogen. Other methods of coupling free amino groups to organic substituents can also be employed to attach the hydrophobic substituent the vancosamine amino group. Thus, reductive alkylation is merely a preferred method of attaching the hydrophobic group to this position of the vancosamine residue, and other methods will be apparent to the person having ordinary skill in the art.

As discussed above, in addition to modifying a glycosidic group to bear at least one hydrophobic substituent as described above in connection with the vancosamine nitrogen, it may also be desirable to modify another glycosidic group to bear a hydrophobic or polar substituent. In fact, any glycosidic group attached to any of the amino acid residues $A_2$–$A_7$ can be modified to bear a hydrophobic substituent in accordance with the present invention. Thus, any of the glycosidic groups in, e.g., the glycopeptide antibiotics vancomycin, eremomycin, chloroeremomycin, and β-avoparcin can be modified to bear at least one hydrophobic substituent. Thus, the present invention is not to be construed as limited to the preferred compounds which comprise a hydrophobic substituent at the vancosamine nitrogen and, optionally, a substituent at the $C_6$ position of the glucose residue directly attached to amino acid $A_4$ in vancomycin.

It is to be understood that where vancomycin is modified to bear a substituent at the $C_6$ position of the glucose residue directly attached to $A_4$, this substituent may be hydrophobic antibiotic which need not be limited to vancomycin, although $C_6$ modification of the glucose residue attached to $A_4$ of vancomycin is preferred. Thus, the following method is particularly suitable for modification of, e.g., a primary hydroxyl group on any glycosidic group attached to any of the amino acid residues $A_2$–$A_7$. Thus, while the foregoing method is described in reference to the primary hydroxyl group at the $C_6$ position of the glucose residue directly attached to $A_4$ of vancomycin, it is to be understood that the synthetic method described below is applicable to any similarly reactive hydroxyl group on any glycosidic group attached to any of the amino acid residues $A_2$–$A_7$. A schematic which generally illustrates the modification of the $C_6$ position of vancomycin is shown below:

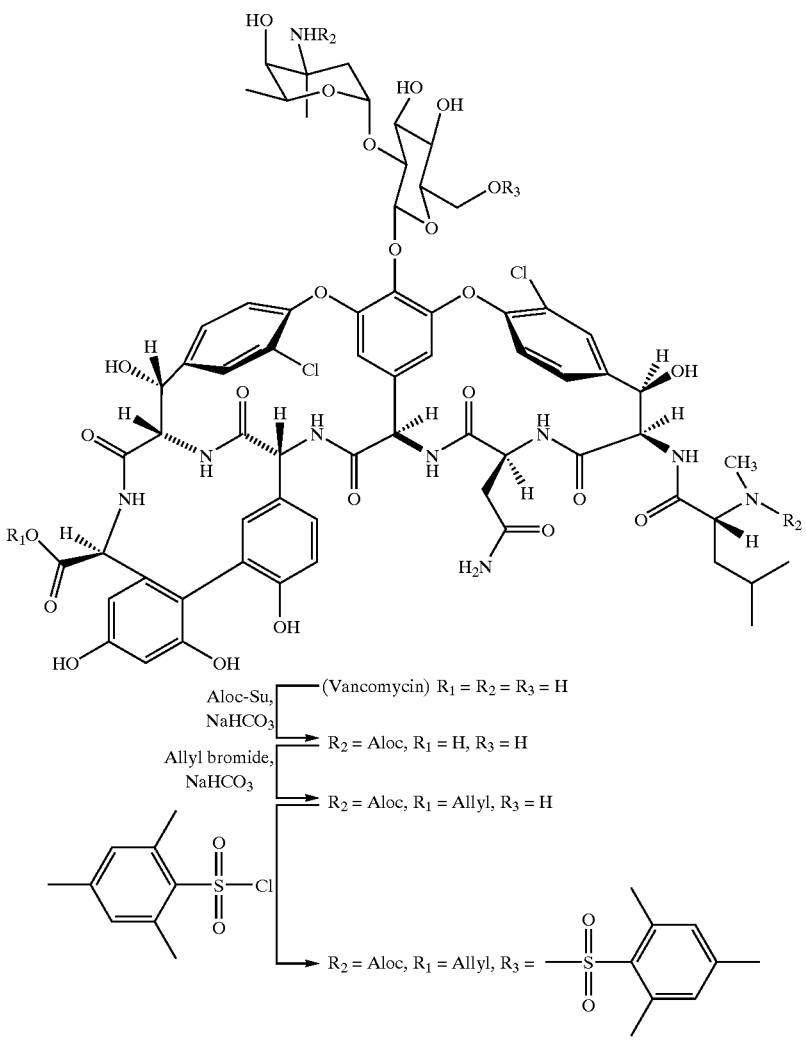

or polar, however, it is preferred that where the vancosamine nitrogen position is modified to bear a hydrophobic substituent, the $C_6$ position, when modified, will preferably be modified to bear a polar substituent. Where the $C_6$ position of glucose attached to $A_4$ of vancomycin is to be modified to bear a substituent, the following strategy may be employed to introduce a suitable set of protecting groups onto vancomycin and to differentiate the $C_6$ hydroxyl group of the glucose residue on $A_4$ of vancomycin from all other hydroxyl groups. This strategy may be generally employed to modify any selected hydroxyl group of a glycopeptide Protection of both amines by similar groups requires using excess acylation reagent while selective protection of the N-methyl leucine residue is known, allowing selective functionalization of the vancosamine amine group. See Pavlov et al., J. Antibiotics, 1993, 46, 1731, incorporated herein in its entirety. Selectively introducing the mesitylenesulfonyl group at the glucose $C_6$ position differentiates this position from the other hydroxyl groups and allows further reaction to displace the mesitylenesulfonyl group, affording may derivatives. A variety of functional groups are introduced at the glucose $C_6$ position by using common methods for nucleophilic displacement of primary arylsulfonyl groups directly, or by further synthetic modification of initial displacement products, including azido and iodo groups. For example, the iodo group is displaced by a variety of nucleophiles to produce additional $C_6$ derivatives. A preferred nucleophile is a thiol compound, especially a heterocyclic thiol. Modification of an azido group at the $C_6$ position is performed, e.g., by reducing the azido group to an amino group, which in turn is functionalized by means of reductive alkylation, nucleophilic substitution, or other amino-group reactions well known to those skilled in the art. In a preferred embodiment of the invention, an azido group is partially reduced by reaction with a phosphine compound to produce an iminophosphorane. In a preferred method of modifying the $C_6$ position, or other similarly reactive hydroxyl group on a glycosidic group, the $C_6$ position is modified to bear a free amino group by displacing the mesitylenesulfonyl group with an azido group which is then reduced to the free amino group. The free amino group at the $C_6$ position can then be further modified to bear, e.g., a hydrophobic substituent by reacting the free amino group in a manner similar to that described above with respect to attaching a hydrophobic substituent to the vancosamine nitrogen.

In the process described above, the vancosamine amino group, the N-methyl leucine amino group and the carboxyl group at $A_7$ of vancomycin are suitably protected. Then, the $C_6$ hydroxyl is substituted with a mesitylenesulfonyl group which, as described above can be further displaced, e.g., by nucleophilic displacement to afford many derivatives. While the above method has been described in connection with attachment of mesitylenesulfonyl group at the $C_6$ position, it is to be understood that after suitably protecting the glycopeptide starting compound, the $C_6$ hydroxyl group can be reacted with any compound that will attach a good leaving group to the $C_6$ position. The leaving group may then be displaced by a subsequent reaction, e.g., by nucleophilic displacement, and further derivatization may then be performed at the $C_6$ position yielding many derivatives. The groups protecting the vancosamine amino group, the N-methyl leucine amino group and the carboxyl group at $A_7$ can be removed in a conventional manner.

Where the $C_6$-substituted vancomycin analog is to be further substituted with a hydrophobic substituent at the vancosamine nitrogen, the protecting groups at the vancosamine amino group, at the carboxyl group at $A_7$ and at the N-methyl lecuine amino group of the $C_6$-substituted vancomycin are removed. The vancosamine nitrogen is then substituted with the hydrophobic substituent in the manner described above, e.g., by performing a reductive alkylation reaction. The N-methyl leucine residue is removed from this compound and the group $A_1$ is attached to the free amino group at $A_2$ as described above. The resulting compound, may then be further modified at the $C_6$ position as described above in connection with the $C_6$ derivatization, thus affording many derivatives. The resultant product, after separation and purification will thus have a hydrophobic substituent at the vancosamnine nitrogen position and will have been modified to bear a group other than hydroxyl at the $C_6$ position of the glucose residue, and will also have an organic group other than N-methyl leucine attached to the amino acid $A_2$.

Preferably, the N-substituted leucine residue is removed from a compound in which one or more of the glycosidic groups attached to one of the amino acid residues $A_2$–$A_7$ is already modified to bear the at least one hydrophobic substituent. However, it is also possible to modify the glycosidic group either prior to or after removal of the N-substituted leucine residue. Thus, it is possible to attach one or more glycosidic groups onto a glycopeptide antibiotic, pseudoaglycone or aglycone bearing a terminal N-substituted leucine residue and then modifying the glycosidic group to bear the at least one hydrophobic substituent. Furthermore, the modification of the glycosidic group can also be conducted either prior to or after attachment of the $A_1$ group upon removal of the terminal N-substituted leucine residue.

The glycosidic group can be attached to any reactive hydroxyl group in a glycopeptide antibiotic, aglycone or pseudoaglycone. Preferably the glycosidic group is attached to an aglycone or to a pseudoaglycone. Where the glycosidic group is attached to an aglycone, it is preferable to attach a second glycosidic group to the previously attached glycosidic group, which results in a disaccharide group attached to one of the amino acid residues in the aglycone. Preferably, the sequential attachment of glycosidic groups is performed at the $A_4$ position of an aglycone, however, it is to be understood that this method can be generally applied to any of the amino acid residues forming an aglycone, pseudoaglycone or glycopeptide antibiotic. The glycosidic groups can be attached to any of the reactive hydroxyl groups in glycopeptide antibiotics, aglycones or pseudoaglycones. These reactive hydroxyl groups are generally phenolic hydroxyl groups, benzylic hydroxyl groups or aliphatic hydroxyl groups. Thus, a glycosidic group can be introduced at any of such hydroxyl groups as desired. Moreover, as discussed above, a glycosidic group can also be attached to a previously attached glycosidic group, which results in a disaccharide group attached to one of the amino acid residues in the aglycone, pseudoaglycone or glycopeptide antibiotic. Any hydroxyl group on the glycopeptide antibiotic, aglycone or pseudoaglycone to which a glycosidic group is not desired to be attached can be suitably protected. Also, the glycosidic group itself may be suitably protected so that the desired glycosidic bond to the glycopeptide antibiotic, aglycone or pseudoaglycone is formed.

Thus, a glycopeptide antibiotic having a terminal N-substituted leucine residue can be prepared by (a) selecting: (i) an aglycone that is soluble in one or more organic solvents, is derived from a glycopeptide antibiotic, and which aglycone has exactly one free phenolic hydroxyl group; and (ii) a protected first glycosyl donor; (b) allowing a non-enzymatic glycosylation reaction to proceed in an organic solvent such that a first glycosidic bond is formed, which links said free phenolic hydroxyl group to the anomeric carbon of the first glycosyl donor to provide a pseudoaglycone having a protected first glycosyl residue; (c) selectively removing one protecting group from the first glycosyl residue to provide a pseudoaglycone bearing exactly one free hydroxyl group on the first glycosyl residue; (d) selecting a second protected glycosyl donor; and (e) allowing a non-enzymatic glycosylation reaction to proceed in an organic solvent such that a second glycosidic bond is formed which links said free hydroxyl group on the pseudoaglycone to the anomeric carbon of the second glycosyl donor. Any of the glycosidic groups on the resultant compound can be modified to bear the at least one hydrophobic substituent in accordance with the preferred methods as described above. Any glycosidic group can be attached to an aglycone, pseudoaglycone or glycopeptide antibiotic in the foregoing manner. Thus, it may be desirable to attach a glycosidic group bearing a free amino group to an aglycone, pseudoaglycone or glycopeptide antibiotic as described above. A hydrophobic substituent can then be attached to the free amino group to produce a compound having a glycosidic group bearing at least one hydrophobic substituent in accordance with the present invention. Attachment of a glycosidic group with a free amino group is advantageous because it may avoid the necessity of functionalizing the glycosidic group to bear an amino group prior to attaching the hydrophobic substituent thereto.

It is apparent that the method described above can be modified by starting with a pseudoaglycone and then attaching another glycosidic group thereto. Thus it is to be understood that the method of suitably protecting and deprotecting hydroxyl groups can be generally applied to selectively attach a glycosidic group to any desired hydroxyl group on an aglycone, pseudoaglycone or glycopeptide antibiotic, any of which may be modified to bear a hydrophobic substituent on a glycosidic group.

Where it is desired to attach glycosidic groups to an aglycone, pseudoaglycone or glycopeptide antibiotic, all reactive functional groups on any of these starting compounds are suitably protected. Thus, amine, carboxylic acid, phenolic and benzylic hydroxyl groups, e.g., need to be protected to avoid their participation in the reaction that attaches the glycosidic group. The protecting groups are suitably chosen so as to render the protected compounds soluble in the reaction medium. The protecting groups may remain on the final compound, but are preferably removed by exposure to acidic or basic conditions, catalytic hydrogenation, or light or other conventional methods for removing protecting groups. Any conventional protecting groups for the functional groups mentioned above may be employed. When the aglycone, pseudoaglycone or glycopeptide antibiotic is or is derived from vancomycin, it is preferred that the protecting groups are as follows: carboxybenzyl (CBz) on the amino nitrogen, a benzyl ester group; benzyl, allyl or methyl phenolic ethers on the phenolic hydroxyls of $A_5$ and $A_7$, and acetates on the aliphatic hydroxyls. Removal of the protective groups can be accomplished by methods well known to the ordinarily skilled organic chemist. Thus, when it is desired to remove protecting groups from any of the compounds of this invention, their removal is accomplished using methods well known to those skilled in the art. The preferred method for removal of protecting groups is as follows. Aloc groups on amines, and allyl esters or allyl ethers are removed by using Pd(0) mediated reactions, e.g., $[Ph_3P]_2Pd(II)Cl_2$ and $Bu_3SnH$ in 1:1 acetic acid:DMF. Acetate protecting groups are removed using hydrazine in THF/methanol. The use of protecting groups to protect any group which might otherwise be reactive under a particular set of reaction conditions is well known to the ordinarily skilled artisan. As will be apparent to the ordinarily skilled artisan, any such conventional protecting groups and the methodologies employed therewith can be used in the present invention.

The suitably protected aglycone, pseudoaglycone or glycopeptide antibiotic is glycosylated via a non-enzymatic reaction in an organic solvent with a variety of glycosyl donors, thereby forming a glycosidic bond between the aglycone, pseudoaglycone, glycopeptide antibiotic and the glycosyl donor. Preferably, the glycosyl donors are activated monosaccharide anomeric sulfoxides which are functionalized at the 6 position or elsewhere. These sulfoxide donors are differentially protected so as to allow for selective deprotection of a single hydroxyl after formation of the glycosidic bond. The single hydroxyl can then be the reactive site for forming another glycosidic bond with a glycosidic group. Suitable protecting groups to allow for this selective deprotection include, but are not limited to, the 2,2-dimethyl acetoacetate group, the 4-azidobutyryl group and any other groups which can be removed in the presence of other protecting groups.

Glycosidic groups can also be removed from a glycopeptide antibiotic or pseudoaglycone. Thus, a glycosidic group can be removed from a glycopeptide antibiotic by (a) selecting a glycopeptide antibiotic that is soluble in one or more organic solvents; (b) contacting the glycopeptide antibiotic with a Lewis acid, and allowing a degradation reaction to proceed such that a sugar residue is removed, producing a pseudoaglycone having exactly one free hydroxyl group on a remaining sugar residue of the pseudoaglycone; a glycosidic group can then optionally be attached to the free hydroxyl group on the pseudoaglycone by the subsequent steps of (c) selecting a protected glycosyl donor; and (d) allowing a non-enzymatic glycosylation reaction to proceed in an organic solvent such that a glycosidic bond is formed which links the free hydroxyl group of the remaining sugar residue on the pseudoaglycone to the anomeric carbon of the glycosyl donor. Thus, the foregoing method can be applied to removal of a glycosidic group, e.g., from a glycopeptide antibiotic having a disaccharide attached to $A_4$. The glycopeptide antibiotic bearing a disaccharide at $A_4$ is treated with a Lewis acid in an organic solvent to remove a sugar residue from the disaccharide group. The Lewis acid is preferably boron trifluoride, preferably as a complex with diethyl ether. When the glycopeptide antibiotic having a disaccharide group at $A_4$ is vancomycin, it is preferred that allyloxycarbonyl (aloc) groups are present on the amines of $A_1$ and the vancosamine residue, acetates on the aliphatic hydroxyl groups, allyl phenyl ethers on the phenolic hydroxyls, and an allyl or o-nitrobenzyl ester on the $A_7$ terminal carboxyl, where a solid-phase synthesis is employed, the o-nitrobenzyl ester is preferred. A degradation reaction then proceeds which remove a glycosidic group to produce a pseudoaglycone in which all reactive functional groups (amine, carboxylic acid, phenols, and benzylic alcohols) are suitably protected except for a hydroxyl group on the remaining glycosidic group attached to residue $A_4$ which is where another glycosidic group can optionally be attached.

Pharmaceutical formulations of the compounds of the present invention are also a part of the present invention, as well as the use of the compounds and formulations thereof to treat infectious diseases in mammals, preferably humans, comprising administering an amount of the compound of the present invention or a pharmaceutically acceptable salt or ester thereof to a mammal, the amount being effective to treat the infectious disease.

Thus, the compounds of the present invention, or pharmaceutically acceptable salts or esters thereof can be formulated for any conventional means of delivery, including oral or parenteral delivery for the therapeutical or prophylactic treatment of infectious diseases, preferably bacterial diseases. The bacterial diseases which may be therapeutically or prophylactically treated with the compounds and/or formulations of the present invention include those caused by Gram-positive and/or Gram-negative microorganisms.

The compounds of the present invention may be administered separately or in combination with any other drug or therapeutic agent. Examples of other therapeutic agents and/or drugs that can be administered with the compounds and/or formulations of the present invention include, but are not limited to, beta lactam antibiotics, such as penems, penams, cephems, carbapenems, oxacephems, carbacephems, and monobactams, or other antibiotics such as cycloserine and fosfomycin. The other therapeutic agent need not be an antibiotic.

The compounds and/or formulations are administered to the mammal in a therapeutically effective amount, which amount is effective to treat, prevent, mitigate and/or alleviate the infectious disease. Thus, the compound of the present invention can be administered to the mammal, preferably a human, in an amount ranging from about 0.5 to about 2 grams per day. The compounds and/or formulations of the present invention can be administered in a single daily dosage or in multiple doses per day. Other periodic treatment protocols may also be adopted. Thus, the treatment protocol may require administration over extended periods of time, e.g., for several days or for from about one to six weeks. The therapeutically effective amounts of the compound of the invention discussed above are merely exemplary. Thus, the amount per administered dose or the total amount administered will depend on such factors as the nature and severity of the infection, the age and general health of the patient, the tolerance of the patient to the compounds and/or formulations of the present invention and the microorganism or microorganisms involved in the infection.

In the pharmaceutical formulations of the present invention, the compound can be admixed with any conventional pharmaceutical carriers and/or excipients and can be formulated for immediate or sustained release. Other time-release profiles, such as combinations of immediate and sustained release are also possible. Thus, the compound of the present invention can be admixed with conventional pharmaceutical carriers and excipients and used in the form of tablets, capsules, caplets, elixirs, suspensions, syrups, wafers and the like. The compounds of the present invention can also be formulated for topical administration. Typical excipients and/or carriers include, but are not limited to corn starch, gelatin, lactose, sucrose, microcrystalline cellulose, kaolin, mannitol, dicalcium phosphate, sodium chloride, and alginic acid. Disintegrators commonly used in the formulations of this invention include croscarmellose sodium, microcrystalline cellulose, corn starch, sodium starch glycolate and alginic acid. Tablet binders that can be included are acacia, methylcellulose, polyvinylpyrrolidone, hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. It may also be desirable to add a coloring agent to make the dosage form more esthetic in appearance or to help identify the product. Tablets may be coated to facilitate swallowing or to modify release of the active compound, or some combination of these.

The compounds and/or formulations can also be administered intravenously or intramuscularly. For intravenous (IV) use, a water-soluble form of the compound is preferably dissolved in one of the commonly used intravenous fluids, and administered by infusion. Such fluids as, for example, physiological saline, Ringer's solution or 5% dextrose can be used. For intramuscular preparations, a sterile formulation of a suitable salt or ester form of the compound of the present invention, for example the hydrochloride salt form can be dissolved and administered in a pharmaceutical diluent such as water-for-injection, physiological saline or 5% glucose solution. A suitable insoluble form of the compound may be prepared and administered as a suspension in an aqueous base or a pharmaceutically acceptable oil base, such as an ester of a long chain fatty acid such as ethyl oleate.

For oral use, a sterile formulation of a suitable salt or ester form of the compound, for example, the hydrochloric acid salt, formulated in a diluent such as distilled or deionized water is particularly useful. Alternatively, the unit dosage form of the compound can be a solution of the compound, preferably in its salt or ester from, in a suitable diluent in sterile, hermetically sealed ampoules.

EXAMPLES

The present invention will now be described with reference to the specific examples below, to which the present invention is not to be construed as limited to.

Example 1 p-chlorobiphenyl vancomycin

The structural formula of p-chlorobiphenyl vancomycin is shown below:

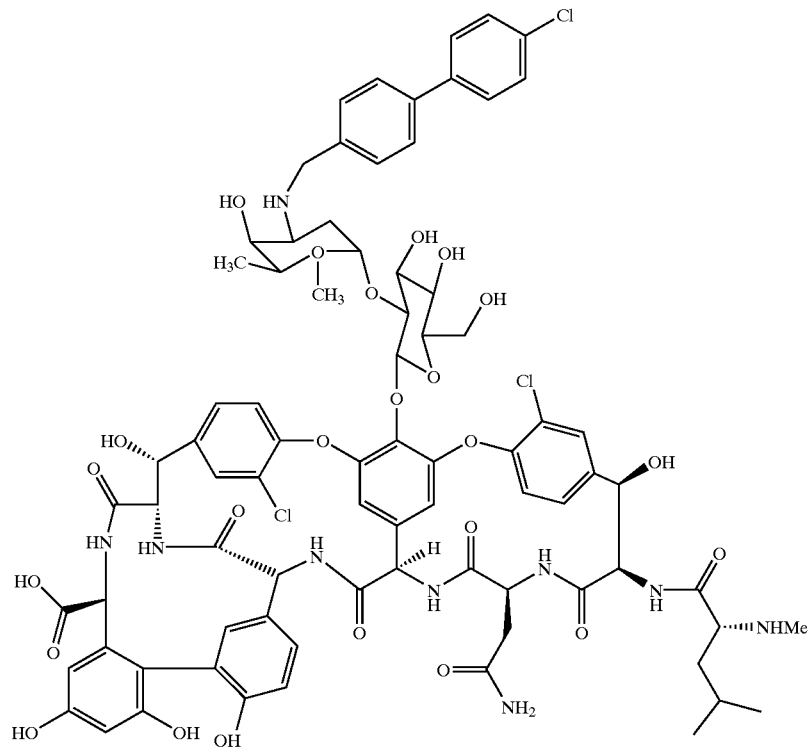

chlorobiphenyl vancomycin
$C_{79}H_{84}Cl_3N_9O_{24}$
Exact Mass: 1647.47
Mol. Wt.: 1649.92

To a solution of vancomycin hydrochloride (20 mg; 13 μmoles) in 1.5 mL DMF was added diisopropylethylamine (11 μL, 65 μmoles) and 4,4'-chlorobiphenylaldehyde (280 μL of a 10 mg/mL solution in DMF; 13 μmoles). The reaction mixture was stirred at 60° C. for half an hour. Sodium cyanoborohydride (77 μL of a 0.5M solution in DMF) was added, and the system was stirred at 60° C. for 1 hour. The reaction mixture was cooled to room temperature and diluted with 25 mL of ethyl ether. The precipitate was collected and purified by reverse phase HPLC:

HPLC conditions for product analysis:

| Column: | Phenomenex C18 column, 21.2 × 250 mm |
|---|---|
| Flow: | 8 mL/min |
| Mobile Phase: | B: acetonitrile |
| | 4: 10 mM ammonium acetate, pH 5.2 |

| Program: | 0 min 30% B |
|---|---|
| | 0.1 min 30% B |
| | 25 min 55% B (linear gradient) |
| | 35 min 90% B (linear gradient) |
| | 35.5 min 90% B (linear gradient) |
| | 45 min 30% B |

Example 2

Des-leucyl p-chlorobiphenyl vancomycin (TS-518)

The structural formula of des-leucyl-p-chlorobiphenyl vancomycin is shown below:

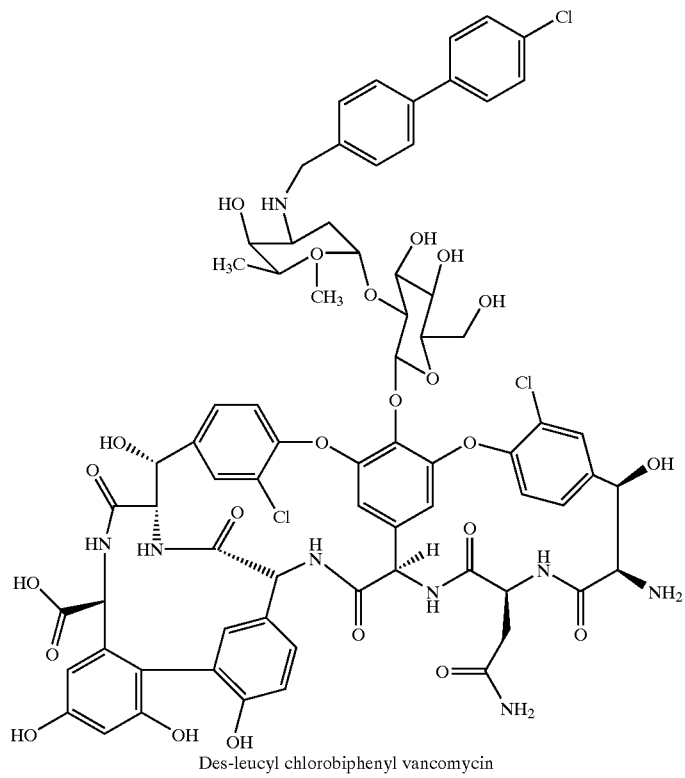

Des-leucyl chlorobiphenyl vancomycin
$C_{72}H_{71}Cl_3N_8O_{23}$
Exact Mass: 1520.37
Mol. Wt.: 1522.73

Under an argon atmosphere, p-chlorobiphenyl vancomycin (130 mg, 7.8 μmoles) was dissolved in 3.4 mL of a 10:10:1 mixture of freshly distilled pyridine, distilled water and triethylamine (99%). Sonication was used to promoted total dissolution. To the colorless solution was added phenyl thioisocyanate (11 μL, 90.1 μmoles), and the system was kept at 50° C. for 20 minutes. The slightly yellow solution was transferred to a separatory funnel, diluted with 10 mL of 10:10:1 pyridine-water-triethylamine solution, and washed with 10 mL of 10% ethyl acetate-hexane. The top layer was discarded. The yellowish bottom layer was transferred to a round-bottom flask, diluted with 5 mL of 2-butanol and concentrated to dryness. The residue was azeotroped twice with toluene. The resulting solid was dissolved in minimal amount of DMF (3 mL) and the product was precipitated by adding a large volume of 50% ethyl acetate-hexane (40 mL). The precipitate was collected by filtration, washed with methylene chloride (3×10 mL) and dried under vacuum to afford a nearly quantitative yield of des-leucyl p-chlorobiphenyl vancomycin (off-white solid). The product may be further purified by flash chromatography on silica gel (3:3:2 ethyl acetate-ethanol-water).

HPLC conditions for product analysis:

| Column: | Nucleosil 4 C18 100 A (250 × 4.6 mm) |
|---|---|
| Flow: | 0.75 mL/min |
| Mobile Phase: | B: acetonitrile |
| | 5: 10 mM ammonium acetate, pH 5.2 |
| Program: | 0 min 25% B |
| | 0.1 min 25% B |
| | 20 min 40% B (linear gradient) |
| | 30 min 90% B (linear gradient) |
| | 30.1 min 25% B (linear gradient) |
| | 40 min 25% B |
| Retention time of product: | 11.6 min. |

Example 3

Compounds were typically prepared in batches of 48. To each of 48 test tubes was added the appropriate carboxylic acid (0.77 mmoles). Bis-(6-carboxy-HOBT)-N-(2-aminoethyl)-aminomethyl polystyrene resin (1.56 mmole/g; purchased from NovaBiochem; 1.19 g) was suspended in 28 ml of amino-free DMF using mild, yet thorough, stirring. An aliquot of the suspension (500 μl) was added to each test tube, followed by 500 μL of amino-free DMF and 100 uL of a solution of 1,3-diisopropyl-carbodiimide in DMF (prepared by adding 750 μoL of 1,3-diisopropyl-carbodiimide to 5 mL of amine-free DMF). The test tubes were shaken on an orbital shaker at 350 rpm for one hour. The supernatant was removed by filtration and discarded. The resin was washed with 2 mL of amine-free DMF (6×).

Des-(N-methyl-leucyl)-p-chlorobiphenyl-vancomycin (1.5 g) was dissolved in 50 mL of amine-Free DMF using sonication. An aliquot of this solution (1 mL) was added to each test tube, followed by 1 mL of amine-Free DMF. The test tubes were shaken on an orbital shaker at 350 rpm for one hour. The supernatant of each reaction mixture was transferred to the well of a labeled 48-well plate. The resin was washed with 1 mL of amine-free DMF (2×) and the washings were combined with the supernatant. In the cases where the carboxylic acid contained an Fmoc group, a 20% solution of piperidine in DMF (1 mL) was added to the corresponding well.

The plates were then dried in a centrifugal evaporator. The residues were treated with 5 mL of DMSO (molecular biology grade) and sonicated until total dissolution. The resulting solutions were used as such for analytical analysis and biological screening.

In the structural formulae in Table I below, "X" designates the —COOH group in the compound that is reacted with the free amino group at $A_2$, forming the new amide linkage.

The antibacterial activity of each of the compounds against the bacterial strains $E.$ $faceium$ (ATCC 49624), $S.$ $epidermidis$ (ATCC 12228), $S.$ $aureus$ (ATCC 29213), $E.$ $faecalis$ (CL 4877) and $E.$ $faecalis$ (ATCC 292121) was tested. Each of the compounds was screened in a 96 will agar array format. Antibacterial activity was referenced to the zones of inhibition observed for p-chlorobiphenylvancomycin. The MIC's of p-chlorobiphenylvancomycin against resistant isolates were approximately 6 ug/ml. A zone score of 2 was assigned when the zone of inhibition for a given compound was equal to the zone generated by the delivery of a 1 mg/ml stock solution of p-chlorobiphenylvancomycin. A zone score of 1 was assigned if the area of the zone was 25% of the area of the zone generated by a 1 mg/ml stock solution of p-chlorobiphenylvancomycin. Likewise a zone score of 3 was assigned if the zone size was 4 times the size of the zone generated by a 1 mg/ml stock solution of p-chlorobiphenylvancomycin. Similarly, a zone score of 4 was assigned if the zone size was 16 times the size of the zone generated by a 1 mg/ml stock solution of p-chlorobiphenylvancomycin and a zone score of 5 was assigned if the zone size was 64 times the size of the zone generated by a 1 mg/ml stock solution of p-chlorobiphenylvancomycin. The screening data for each of the compounds is presented in Table I, below.

TABLE I

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 1 | ALA | | 2 | 4 | 4 | 4 | 1 |
| 2 | ASN(TRT) | | 1 | 1 | 1 | 2 | 1 |
| 3 | ASP(OTBU) | | 1 | 3 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 4 | CHA | | 1 | 3 | 2 | 2 | 1 |
| 5 | CIS | | 2 | 3 | 3 | 2 | 1 |
| 6 | CYC(MMT) | | 1 | 1 | 1 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 7 | PHE | | 1 | 3 | 2 | 2 | 1 |
| 8 | SAR | | 3 | 4 | 4 | 2 | 2 |
| 9 | SER(TRT) | | 1 | 1 | 1 | 1 | 1 |
| 10 | THI | | 2 | 3 | 2 | 3 | 1 |

TABLE I-continued
Side Chains attached to Free Amino Group at A₂ of des-leucyl-p-chlorobiphenyl vancomycin and Biological Screening Results
| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 11 | THR(TRT) | 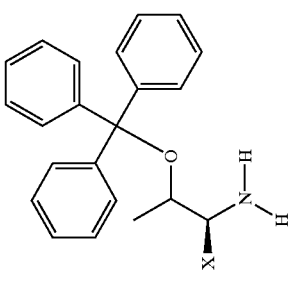 | 1 | 1 | 1 | 2 | 1 |
| 12 | TRP | 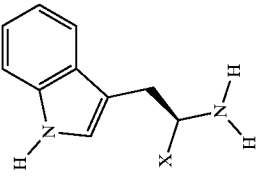 | 1 | 2 | 2 | 4 | 1 |
| 13 | CYS(TRT) | 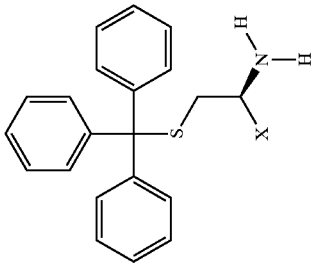 | 1 | 1 | 1 | 1 | 1 |

TABLE I-continued
Side Chains attached to Free Amino Group at A₂ of des-leucyl-p-chlorobiphenyl vancomycin and Biological Screening Results
| Cmpd No. | Reagent Name | | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 14 | D-CYS(TRT) | | 1 | 1 | 1 | 2 | 1 |
| 15 | D-MET | 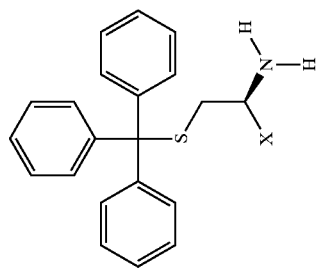 | 4 | 5 | 5 | 2 | 4 |
| 16 | D-PHE | 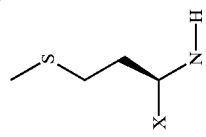 | 3 | 5 | 4 | 3 | 3 |
| 17 | D-SER(TBU) | 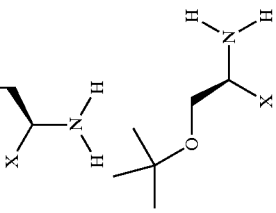 | 5 | 5 | 5 | 5 | 5 |

TABLE I-continued

Side Chains attached to Free Amino Group at A₂ of des-leucyl-p-chlorobiphenyl vancomycin and Biological Screening Results

| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 18 | | | 2 | 3 | 2 | 3 | 1 |
| 19 | | TYR(TBU) | 1 | 3 | 2 | 3 | 1 |
| 20 | | VAL | 2 | 4 | 3 | 4 | 1 |
| 21 | | L-(+)-LACTIC ACID | 1 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 22 | MYR-GLY | 1 | 2 | 2 | 3 | 1 |
| 23 | (R,S)-2-CARBOXY-MORPHOLINE | 1 | 2 | 2 | 2 | 1 |
| 24 | 4-PIPERAZIN-1-YL ACETIC ACID | 2 | 2 | 3 | 4 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 25 | D-TRP | 2 | 4 | 2 | 2 | 2 |
| 26 | GLU(OBZL) | 1 | 3 | 2 | 2 | 1 |
| 27 | GLN(TRT) | 1 | 1 | 1 | 3 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 28 | GLY | 2 | 4 | 3 | 2 | 2 |
| 29 | HIS(TRT) | 1 | 1 | 1 | 1 | 1 |
| 30 | HYP(TBU) | 2 | 4 | 3 | 5 | 1 |
| 31 | (3S,4S)-4-AMINO-3-HYDROXY-6-METHYLTHIO-HEXANOIC ACID | 1 | 2 | 2 | 1 | 1 |

TABLE I-continued

Side Chains attached to Free Amino Group at A₇ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 32 | 3-AMINO-1-CARBOXY METHYL-PYRIDIN-2-ONE | 2 | 3 | 2 | 2 | 1 |
| 33 | 4-(2-AMINOETHYL)-1-CARBOXY METHYL-PIPERAZINE DIHYDRO CHLORIDE | 2 | 3 | 2 | 2 | 1 |
| 34 | 2-CARBOXY METHYL-PIPERAZINE | 2 | 3 | 4 | 5 | 1 |
| 35 | ALA-ALA | 1 | 2 | 2 | 2 | 1 |
| 36 | ALA-GLY | 2 | 4 | 4 | 5 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 37 | ILE | 1 | 3 | 3 | 5 | 1 |
| 38 | LEU | 2 | 4 | 2 | 1 | 1 |
| 39 | LYS(DDE) | 1 | 3 | 2 | 2 | 1 |
| 40 | LYS(MTT) | 1 | 1 | 1 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 41 | MET | | 2 | 4 | 3 | 2 | 1 |
| 42 | NLE | | 2 | 4 | 4 | 5 | 1 |
| 43 | ALLO-THR | | 2 | 3 | 4 | 2 | 1 |
| 44 | ASN(GLCNAC(AC)3-BETA-D) | | 1 | 1 | 1 | 1 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 45 | ASN(TMOB) | 1 | 2 | 2 | 2 | 1 |
| 46 | BETA, BETA-DIMETHYL-D-CYS (ACM) | 4 | 5 | 5 | 2 | 4 |
| 47 | BETA-ALA | 2 | 4 | 3 | 2 | 1 |
| 48 | CYS(2-HYDROXY ETHYL) | 1 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 49 | CYS(ACM) | 1 | 4 | 2 | 2 | 1 |
| 50 | CYS(ME) | 2 | 4 | 1 | 2 | 1 |
| 51 | D-ALA | 4 | 5 | 5 | 2 | 4 |
| 52 | D-ALLO-THR | 3 | 4 | 4 | 1 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 53 | D-ASN | | 1 | 2 | 4 | 2 | 1 |
| 54 | D-CIS-HYP | | 1 | 2 | 2 | 2 | 1 |
| 55 | D-CYS(ACM) | | 3 | 4 | 4 | 2 | 1 |
| 56 | D-DPR(DDE) | | 2 | 4 | 3 | 3 | 1 |

TABLE I-continued

Side Chains attached to Free Amino Group at A₂ of des-leucyl-p-chlorobiphenyl vancomycin and Biological Screening Results

| Cmpd No. | Reagent Name | | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 57 | D-GLN | | 2 | 4 | 3 | 3 | 2 |
| 58 | D-HIS | | 1 | 1 | 1 | 2 | 1 |
| 59 | D-ISO ASPARAGINE | | 1 | 2 | 2 | 2 | 1 |
| 60 | DL-ISOSER | | 1 | 1 | 1 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 61 | D-LYS(CARBAMYL) | 4 | 5 | 5 | 3 | 4 |
| 62 | D-ORN(CARBAMYL) | 4 | 5 | 4 | 4 | 4 |
| 63 | D-SER | 3 | 4 | 2 | 2 | 1 |
| 64 | D-THR | 4 | 5 | 4 | 2 | 2 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 65 | GAMMA-ABU | 1 | 2 | 2 | 2 | 1 |
| 66 | GLN(TMOB) | 1 | 2 | 2 | 2 | 1 |
| 67 | GLY-GLY-GLY | 1 | 2 | 2 | 4 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 68 | GLY-GLY | | 2 | 3 | 3 | 5 | 1 |
| 69 | GLY-PRO-HYP | | 1 | 1 | 1 | 2 | 1 |
| 70 | GLY-VAL | | 1 | 1 | 1 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 71 | HIS | | 1 | 1 | 1 | 2 | 1 |
| 72 | HYP | | 2 | 2 | 3 | 2 | 1 |
| 73 | L-ASPARAGINE | | 1 | 1 | 1 | 1 | 1 |
| 74 | L-ISO ASPARAGINE | | 1 | 2 | 2 | 1 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 75 | L-LYS(BIOTIN) | | 2 | 2 | 1 | 2 | 2 |
| 76 | LYS(AC) | | 2 | 2 | 1 | 1 | 1 |
| 77 | LYS(BIOTINYL-EPSILON-AMINOCARPROYL) | | 1 | 1 | 1 | 5 | 1 |

TABLE I-continued

Side Chains attached to Free Amino Group at A, of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 78 | LYS(CARBAMYL) | 1 | 2 | 2 | 1 | 1 |
| 79 | LYS(FOR) | 2 | 3 | 2 | 5 | 1 |
| 80 | LYS(ME)3 CHLORIDE | 2 | 4 | 2 | 5 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 81 | MET(O) | 2 | 2 | 3 | 5 | 1 |
| 82 | MET(O2) | 2 | 3 | 3 | 4 | 1 |
| 83 | ORN(PYRAZINYL CARBONYL) | 2 | 3 | 2 | 4 | 1 |
| 84 | PEN(ACM) | 2 | 2 | 2 | 1 | 1 |

TABLE I-continued
Side Chains attached to Free Amino Group at A₂ of des-leucyl-p-chlorobiphenyl vancomycin and Biological Screening Results
| Cmpd No. | | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 85 | 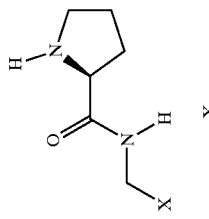 | PRO-GLY | 2 | 2 | 2 | 2 | 1 |
| 86 | 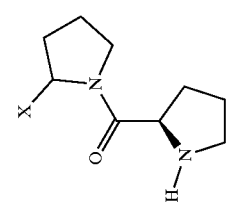 | PRO-PRO | 1 | 2 | 2 | 2 | 1 |
| 87 | 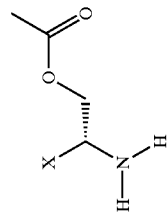 | SER(AC) | 1 | 2 | 2 | 2 | 1 |
| 88 | 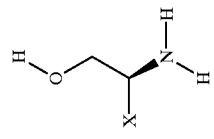 | SER | 2 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 89 | | THR | 2 | 2 | 1 | 2 | 1 |
| 90 | | N-ALPHA-L-ARGININE | 1 | 1 | 2 | 2 | 1 |
| 91 | | N-ALPHA-L-GLUTAMINE | 1 | 2 | 3 | 5 | 1 |
| 92 | | N-ALPHA-N-BETA-ALOC-L-DIAMINO PROPIONIC ACID | 1 | 3 | 3 | 2 | 1 |

TABLE I-continued

Side Chains attached to Free Amino Group at A, of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 93 | N-ALPHA-N-GAMMA-ALLOC-L-DIAMINO BUTYRIC ACID | 1 | 2 | 2 | 3 | 1 |
| 94 | (2-CARBOXY ETHYL) DIMETHYL SULFONIUM CHLORIDE | 1 | 2 | 2 | 2 | 1 |
| 95 | (3-ACETYL-2-METHYL-5-OXO-2-PYRROLIN-4-YL) ACETIC ACID | 1 | 1 | 1 | 3 | 1 |
| 96 | (S)-(−)-4-OXO-2-AZETIDINE CARBOXYLIC ACID | 1 | 1 | 1 | 2 | 1 |
| 97 | [3-METHYOXY CARBONYL]-2-METHYL-5-OXO-2-PYRROLIN-4-YL]ACETIC ACID | 1 | 1 | 1 | 1 | 1 |

TABLE I-continued

Side Chains attached to Free Amino Group at A, of des-leucyl-p-chlorobiphenyl vancomycin and Biological Screening Results

| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 98 | | 1-(AMINO CARBONYL)-1-CYCLOPROPANE CARBOXYLIC ACID | 1 | 1 | 2 | 2 | 1 |
| 99 | | 1-ACETYL PIPERIDINE-4-CARBOXYLIC ACID | 1 | 2 | 3 | 1 | 1 |
| 100 | | 2-(2-METHOXY ETHOXY) ACETIC ACID | 1 | 1 | 2 | 3 | 1 |
| 101 | | 2-[2-(2-METHOXY ETHOXY) ETHOXY]ACETIC ACID | 1 | 1 | 1 | 2 | 1 |
| 102 | | 2-ACETAMIDO ACRYLIC ACID | 1 | 1 | 1 | 2 | 1 |

TABLE I-continued

Side Chains attached to Free Amino Group at A, of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 103 | 2-PYRAZINE CARBOXYLIC ACID | | 1 | 1 | 1 | 2 | 1 |
| 104 | 3,4-DIACETAMIDO BENZOIC ACID | | 1 | 1 | 2 | 2 | 1 |
| 105 | 3-AMINO PYRAZINE-2-CARBOXYLIC ACID | | 1 | 1 | 1 | 2 | 1 |
| 106 | 3-HYDROXY PROPIONIC ACID | | 1 | 2 | 2 | 2 | 1 |
| 107 | 4-ACETAMIDO BUTYRIC ACID | | 1 | 1 | 2 | 2 | 1 |

TABLE I-continued

Side Chains attached to Free Amino Group at A₂ of des-leucyl-p-chlorobiphenyl vancomycin and Biological Screening Results

| Cmpd No. | | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 108 | | 4-NITRO BENZOYL-GLYCYL-GLYCINE | 1 | 1 | 2 | 4 | 1 |
| 109 | | 5-AMINOOROTIC ACID | 1 | 1 | 2 | 1 | 1 |
| 110 | | AC-ALA | 1 | 1 | 2 | 2 | 1 |
| 111 | | AC-ARG | 1 | 1 | 1 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 112 | AC-D-ALA | | 1 | 1 | 2 | 4 | 1 |
| 113 | AC-D-ASN | | 1 | 1 | 1 | 2 | 1 |
| 114 | AC-DL-LYS(AC) | | 1 | 1 | 1 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 115 | AC-D-MET | | 1 | 1 | 2 | 2 | 1 |
| 116 | AC-D-PRO | | 1 | 2 | 2 | 2 | 1 |
| 117 | ACETOXYACETIC ACID | | 1 | 2 | 2 | 1 | 1 |
| 118 | ACETYL-DL-CARNITINE HYDROCHLORIDE | | 1 | 2 | 2 | 4 | 1 |
| 119 | ACETYL-L-CARNITINE-HYDROCHLORIDE | | 1 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 120 | AC-GLY-GLY | | 1 | 2 | 2 | 2 | 1 |
| 121 | AC-HYP | | 1 | 1 | 2 | 2 | 1 |
| 122 | AC-LEU-GLY | | 1 | 1 | 1 | 1 | 1 |
| 123 | AC-LYS(AC) | | 1 | 1 | 2 | 1 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 124 | AC-MET(O) | | 1 | 1 | 2 | 4 | 1 |
| 125 | AC-THR | | 1 | 1 | 1 | 2 | 1 |
| 126 | ALLANTOIC ACID | | 1 | 1 | 1 | 2 | 1 |
| 127 | ARABIC ACID | | 1 | 1 | 1 | 2 | 1 |

TABLE I-continued

Side Chains attached to Free Amino Group at A₇ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 128 | ARABINIC ACID | 1 | 1 | 2 | 1 | 1 |
| 129 | BETAINE HYDROCHLORIDE | 1 | 2 | 1 | 2 | 1 |
| 130 | BICINE | 1 | 1 | 2 | 2 | 1 |
| 131 | BOC-ALA-GLY-GLY | 1 | 1 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 132 | BOC-ALA-GLY-SAR | 1 | 1 | 2 | 2 | 1 |
| 133 | BOC-ASN | 1 | 1 | 1 | 2 | 1 |
| 134 | BOC-ASP-NH2 | 1 | 2 | 3 | 2 | 1 |

TABLE I-continued

Side Chains attached to Free Amino Group at A₇ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 135 | BOC-D-ASN | 1 | 2 | 2 | 3 | 1 |
| 136 | BOC-D-GLN | 1 | 2 | 1 | 4 | 1 |
| 137 | BOC-GLU-NH2 | 1 | 1 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 138 | BOC-GLY-ARG | 1 | 1 | 1 | 2 | 1 |
| 139 | BOC-GLY-GLY-GLY | 1 | 1 | 2 | 2 | 1 |
| 140 | BOC-GLY-GLY | 1 | 1 | 1 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 141 | BOC-L-GLUTAMINE | 1 | 1 | 2 | 2 | 1 |
| 142 | BOC-MET(O) | 2 | 1 | 2 | 2 | 1 |
| 143 | BOC-MET(O2) | 1 | 1 | 2 | 1 | 1 |

TABLE I-continued
Side Chains attached to Free Amino Group at $A_2$ of des-leucyl-p-chlorobiphenyl vancomycin and Biological Screening Results
| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 144 | CACOTHELINE | 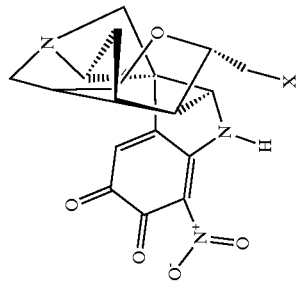 | 1 | 1 | 1 | 2 | 1 |
| 145 | CREATINE | 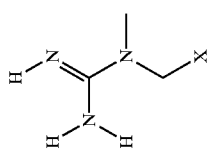 | 1 | 1 | 1 | 2 | 1 |
| 146 | D-(−)-QUINIC ACID | 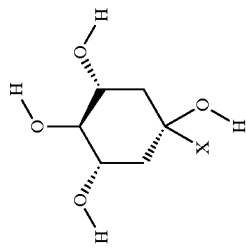 | 1 | 1 | 1 | 2 | 1 |

TABLE I-continued

Side Chains attached to Free Amino Group at A, of des-leucyl-p-chlorobiphenyl vancomycin and Biological Screening Results

| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 147 | | D-(+)GALACTURONIC ACID MONOHYDRATE | 1 | 1 | 1 | 2 | 1 |
| 148 | | D-ALPHA-GALACTURONIC ACID | 1 | 1 | 1 | 2 | 1 |
| 149 | | D-CARNITINE HYDROCHLORIDE | 2 | 1 | 1 | 2 | 1 |
| 150 | | D-GLUCURONIC ACID | 1 | 1 | 1 | 1 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 151 | DL-CARNITINE HYDROCHLORIDE | | 2 | 2 | 4 | 2 | 1 |
| 152 | DL-GLYCERIC ACID | | 1 | 1 | 1 | 2 | 1 |
| 153 | DL-PYRO GLUTAMIC ACID | | 1 | 1 | 1 | 1 | 1 |
| 154 | D-PYRO GLUTAMIC ACID | | 1 | 1 | 1 | 1 | 1 |
| 155 | D-SACCHARIC ACID 1,4-LACTONE | | 1 | 1 | 1 | 2 | 1 |

TABLE I-continued
Side Chains attached to Free Amino Group at A₂ of des-leucyl-p-chlorobiphenyl vancomycin and Biological Screening Results
| Cmpd No. | | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 156 | 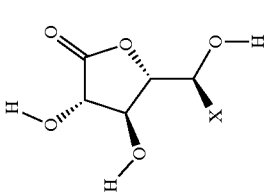 | D-SACCHARIC ACID 3,6-LACTONE | 1 | 1 | 1 | 1 | 1 |
| 157 | 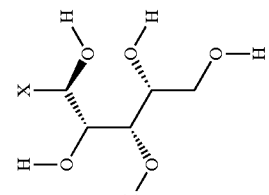 | GLUCONIC ACID | 1 | 1 | 2 | 2 | 1 |
| 158 | 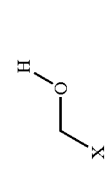 | GLYCOLIC ACID | 1 | 2 | 2 | 2 | 1 |
| 159 | 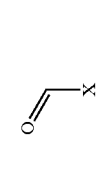 | GLYOXYLIC ACID | 1 | 1 | 1 | 2 | 1 |
| 160 | 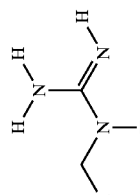 | GUANIDOACETIC ACID | 1 | 1 | 1 | 1 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 161 | HIPPURYL-GLY-GLY-OH | 1 | 1 | 1 | 2 | 1 |
| 162 | HYDANTOIC ACID | 1 | 1 | 1 | 2 | 1 |
| 163 | HYDANTOIN-5-ACETIC ACID | 1 | 1 | 2 | 1 | 1 |
| 164 | LACTOBIONIC ACID | 1 | 1 | 1 | 1 | 1 |

TABLE I-continued

Side Chains attached to Free Amino Group at A₂ of des-leucyl-p-chlorobiphenyl vancomycin and Biological Screening Results

| Cmpd No. | | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 165 | | L-ARGININIC ACID | 1 | 1 | 1 | 2 | 1 |
| 166 | | L-BETA-IMIDAZO LELACTIC ACID | 1 | 1 | 1 | 1 | 1 |
| 167 | | L-CARNITINE HYDROCHLORIDE | 1 | 1 | 1 | 1 | 1 |

TABLE I-continued

Side Chains attached to Free Amino Group at A, of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 168 | L-DIHYDRO OROTIC ACID | 1 | 1 | 1 | 2 | 1 |
| 169 | L-PYRO GLUTAMIC ACID | 1 | 1 | 1 | 2 | 1 |
| 170 | MALEAMIC ACID | 1 | 2 | 1 | 2 | 1 |
| 171 | METHANE SULFONYL ACETIC ACID | 1 | 1 | 1 | 2 | 1 |
| 172 | N-(ACETO ACETYL) GLYCINE | 1 | 1 | 1 | 2 | 1 |
| 173 | N,N-DIMETHYL SUCCINAMIC ACID | 1 | 1 | 1 | 1 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 174 | N-ACETYL-DL-ALANINE | | 1 | 1 | 1 | 2 | 1 |
| 175 | N-ACETYL-DL-METHIONINE | | 1 | 2 | 2 | 1 | 1 |
| 176 | N-ACETYL-DL-PROLINE | | 1 | 2 | 2 | 2 | 1 |
| 177 | N-ACETYL-DL-PROPARGYL-GLYCINE | | 1 | 1 | 2 | 2 | 1 |

TABLE I-continued

Side Chains attached to Free Amino Group at A, of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 178 | N-ACETYL-DL-SERINE | 1 | 1 | 1 | 2 | 1 |
| 179 | N-ACETYL GLYCINE | 1 | 1 | 1 | 2 | 1 |
| 180 | N-ACETYL-L-GLUTAMINE | 1 | 1 | 1 | 1 | 1 |
| 181 | N-ACETYL-L-HISTIDINE | 1 | 2 | 2 | 2 | 1 |

TABLE I-continued
Side Chains attached to Free Amino Group at A, of des-leucyl-p-chlorobiphenyl vancomycin and Biological Screening Results
| Cmpd No. | | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 182 | 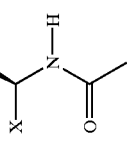 | N-ACETYL-L-METHIONINE | 1 | 2 | 1 | 2 | 1 |
| 183 | 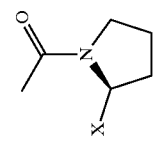 | N-ACETYL-L-PROLINE | 1 | 2 | 2 | 2 | 1 |
| 184 | 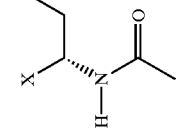 | N-ALPHA-ACETYL-L-ARGININE DIHYDRATE | 1 | 1 | 1 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 185 | N-ALPHA-ACETYL-L-ASPARAGINE | | 1 | 1 | 1 | 1 | 1 |
| 186 | BETA-GUANIDINO PROPIONIC ACID | | 1 | 1 | 1 | 1 | 1 |
| 187 | N-ALPHA-CARBAMYL-L-ARGININE | | 1 | 1 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 188 | N-ALPHA-CARBOETHOXY-L-ASPARAGINE | 1 | 1 | 2 | 2 | 1 |
| 189 | N-CARBAMOYL MALEAMIC ACID | 1 | 1 | 2 | 2 | 1 |
| 190 | N-CARBAMYL-ALPHA-AMINO-ISOBUTYRIC ACID | 1 | 1 | 2 | 3 | 1 |
| 191 | N-CARBAMYL-DL-ALPHA-AMINO-N-BUTYRIC ACID | 1 | 1 | 1 | 3 | 1 |

TABLE I-continued

Side Chains attached to Free Amino Group at A₂ of des-leucyl-p-chlorobiphenyl vancomycin and Biological Screening Results

| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 192 | | N-CARBAMYL-L-HISTIDINE HYDROCHLORIDE | 1 | 1 | 1 | 2 | 1 |
| 193 | | N-FORMYL GLYCINE | 1 | 2 | 3 | 2 | 1 |
| 194 | | N-FORMYL-L-ALANINE | 1 | 1 | 2 | 2 | 1 |
| 195 | | N-FORMYL-L-HISTIDINE | 1 | 2 | 2 | 2 | 1 |

TABLE I-continued
Side Chains attached to Free Amino Group at A₂ of des-leucyl-p-chlorobiphenyl vancomycin and Biological Screening Results
| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 196 | N-FORMYL-L-METHIONINE | 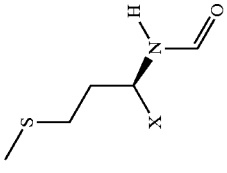 | 1 | 1 | 2 | 3 | 1 |
| 197 | NICOTINURIC ACID | 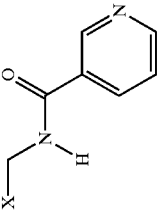 | 1 | 1 | 2 | 2 | 1 |
| 198 | OROTIC ACID | 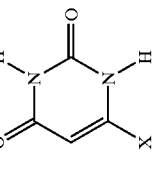 | 1 | 2 | 2 | 3 | 1 |
| 199 | OXALYL MONOGUANYL HYDRAZIDE | 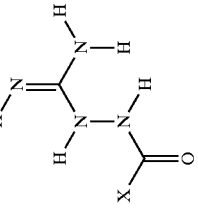 | 1 | 1 | 2 | 2 | 1 |
| 200 | OXAMIC ACID | 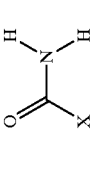 | 1 | 1 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 201 | SHIKIMIC ACID | | 1 | 1 | 2 | 2 | 1 |
| 202 | SUCCINAMIC ACID | | 1 | 2 | 2 | 2 | 1 |
| 203 | SUCCINIC ACID 2,2-DIMETHYL HYDRAZIDE | | 1 | 1 | 2 | 1 | 1 |
| 204 | SUCCINIC SEMIALDEHYDE | | 1 | 1 | 2 | 2 | 1 |
| 205 | SULFOACETIC ACID | | 1 | 1 | 2 | 2 | 1 |
| 206 | DL-2-UREIDO PROPIONIC ACID | | 1 | 2 | 2 | 2 | 1 |

TABLE I-continued

Side Chains attached to Free Amino Group at A₇ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 207 | THYMINE-1-ACETIC ACID | 1 | 2 | 4 | 3 | 1 |
| 208 | URACIL-5-CARBOXYLIC ACID | 1 | 1 | 2 | 2 | 1 |
| 209 | Z-ALA-GLY-GLY | 1 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 210 | Z-BETA-ALA-GLY-GLY | 1 | 2 | 2 | 2 | 1 |
| 211 | Z-GLN-GLY | 1 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 212 | Z-GLY-GLN | 1 | 2 | 2 | 2 | 1 |
| 213 | Z-GLY-GLY-ALA | 1 | 2 | 2 | 2 | 1 |

TABLE I-continued
Side Chains attached to Free Amino Group at $A_7$ of des-leucyl-p-chlorobiphenyl vancomycin and Biological Screening Results
| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 214 | Z-GLY-GLY-GLY-GLY (SEQ. ID NO: 1) | 1 | 1 | 2 | 2 | 1 |
| 215 | Z-GLY-GLY-GLY | 1 | 1 | 2 | 2 | 1 |
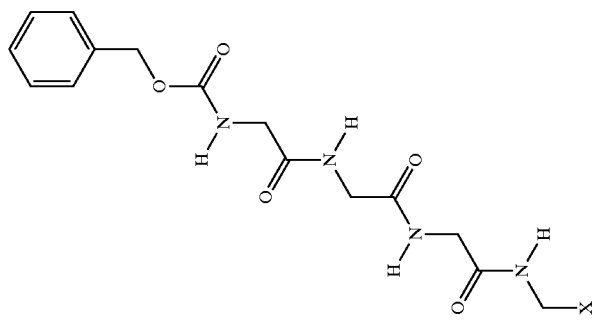
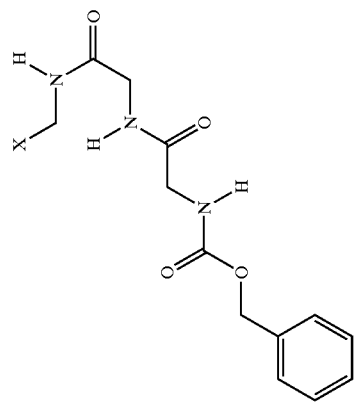

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 216 | DELTA-VAL | 1 | 1 | 2 | 1 | 1 |
| 217 | D-ARG | 2 | 3 | 3 | 2 | 1 |
| 218 | ACPC | 1 | 1 | 2 | 1 | 1 |
| 219 | DELTA-ABU | 1 | 1 | 2 | 2 | 1 |
| 220 | ALA | 2 | 4 | 4 | 1 | 1 |

TABLE I-continued

Side Chains attached to Free Amino Group at A₂ of des-leucyl-p-chlorobiphenyl vancomycin and Biological Screening Results

| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 221 | | 3-UREIDO PROPIONIC ACID | 1 | 1 | 2 | 2 | 1 |
| 222 | | CARBOXY METHYL AMINE HEMIHYDRO CHLORIDE | 1 | 1 | 2 | 2 | 1 |
| 223 | | BOC-GLN-GLN-OH | 1 | 1 | 2 | 2 | 1 |
| 224 | | (−)-2-OXO-4-THIAZOLIDINE-CARBOXYLIC ACID | 1 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 225 |  | (ETHYLTHIO) ACETIC ACID | 1 | 3 | 4 | 2 | 1 |
| 226 |  | (METHYLTHIO) ACETIC ACID | 1 | 2 | 4 | 1 | 1 |
| 227 |  | (R)-(−)-5-OXO-2-TETRAHYDRO FURAN CARBOXYLIC ACID | 1 | 2 | 2 | 1 | 1 |
| 228 | 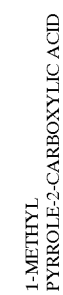 | 1H-TETRAZOLE-1-ACETIC ACID | 1 | 2 | 1 | 2 | 1 |
| 229 | 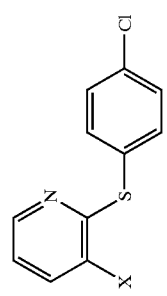 | 1-METHYL PYRROLE-2-CARBOXYLIC ACID | 1 | 2 | 2 | 2 | 1 |
| 230 |  | 2-(4-CHLORO PHENYLTHIO) NICOTINIC ACID | 1 | 1 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 231 | 2-(TRIFLUORO METHYL) PROPENOIC ACID | 1 | 1 | 2 | 2 | 1 |
| 232 | 2,2-BIS(HYDROXY METHYL) PROPIONIC ACID | 1 | 1 | 2 | 2 | 1 |
| 233 | 2,4,5-TRICHLORO PHENOXY ACETIC ACID | 1 | 1 | 2 | 2 | 1 |
| 234 | 2,4-DICHLORO PHENYLACETIC ACID | 1 | 2 | 2 | 2 | 1 |
| 235 | 2,4-DIHYDROXY BENZOIC ACID | 1 | 1 | 1 | 1 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 236 | 2,4-DIMETHOXY BENZOIC ACID | 1 | 1 | 2 | 2 | 1 |
| 237 | 2-AMINO NICOTINIC ACID | 1 | 2 | 4 | 2 | 1 |
| 238 | 2-FLUORO BENZOIC ACID | 1 | 2 | 2 | 2 | 1 |
| 239 | 2-FURAN GLYOXYLIC ACID | 1 | 1 | 2 | 1 | 1 |
| 240 | 2-FUROIC ACID | 1 | 2 | 2 | 1 | 1 |
| 241 | 2-HYDROXY NICOTINIC ACID | 1 | 1 | 1 | 2 | 1 |

TABLE I-continued

Side Chains attached to Free Amino Group at A₂ of des-leucyl-p-chlorobiphenyl vancomycin and Biological Screening Results

| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 242 | | 2-KETOBUTYRIC ACID | 1 | 1 | 1 | 2 | 1 |
| 243 | | 2-METHYL PYRAZINE-5-CARBOXYLIC ACID | 1 | 1 | 2 | 2 | 1 |
| 244 | | 3-(2-FURYL) ACRYLIC ACID | 1 | 2 | 2 | 3 | 1 |
| 245 | | 3-(3,4-DIMETHOXYL PHENYL) PROPIONIC ACID | 1 | 2 | 2 | 2 | 1 |
| 246 | | 3-(PHENYL SULFONYL) PROPIONIC ACID | 2 | 4 | 5 | 3 | 1 |

TABLE I-continued

Side Chains attached to Free Amino Group at A, of des-leucyl-p-chlorobiphenyl vancomycin and Biological Screening Results

| Cmpd No. | | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 247 | | 3-(TRIFLUORO METHYL) BENZOIC ACID | 1 | 2 | 3 | 2 | 1 |
| 248 | | 3-(TRIFLUORO METHYLTHIO) BENZOIC ACID | 1 | 1 | 2 | 2 | 1 |
| 249 | | 3,3,3-TRIFLUORO PROPIONIC ACID | 1 | 3 | 4 | 2 | 1 |
| 250 | | 3,4,5-TRIACETOXY BENZOIC ACID | 1 | 2 | 3 | 1 | |

TABLE I-continued

Side Chains attached to Free Amino Group at A₂ of des-leucyl-p-chlorobiphenyl vancomycin and Biological Screening Results

| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 251 | | 3,4-DICHLORO CINNAMIC ACID | 1 | 1 | 1 | 2 | 1 |
| 252 | | 3,4-DIFLUORO PHENYLACETIC ACID | 1 | 2 | 4 | 1 | 1 |
| 253 | | 3,4-DIMETHOXY BENZOIC ACID | 1 | 2 | 2 | 2 | 1 |
| 254 | | 3,5-BIS(TRIFLUORO METHYL) BENZOIC ACID | 1 | 1 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 255 | 3,5-DIHYDROXY BENZOIC ACID | | 1 | 1 | 2 | 2 | 1 |
| 256 | 3-AMINO-1,2,4-TRIAZOLE-5-CARBOXYLIC ACID | | 1 | 1 | 2 | 2 | 1 |
| 257 | 3-AMINOBENZOIC ACID | | 1 | 2 | 2 | 2 | 1 |
| 258 | 3-ETHOXY PROPIONIC ACID | | 1 | 2 | 2 | 2 | 1 |
| 259 | 3-FLUORO BENZOIC ACID | | 1 | 2 | 3 | 1 | 1 |

TABLE I-continued

Side Chains attached to Free Amino Group at A₂ of des-leucyl-p-chlorobiphenyl vancomycin and Biological Screening Results

| Cmpd No. | Reagent Name | | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 260 | 3-FUROIC ACID | | 1 | 2 | 3 | 1 | 1 |
| 261 | 3-HYDROXY BENZOIC ACID | | 1 | 2 | 2 | 2 | 1 |
| 262 | 3-HYDROXY BUTYRIC ACID | | 1 | 2 | 2 | 2 | 1 |
| 263 | 3-METHYL THIOPROPIONIC ACID | | 1 | 4 | 5 | 1 | 1 |
| 264 | 4-(METHYL SULFONYL) BENZOIC ACID | | 1 | 2 | 2 | 0 | 1 |

TABLE I-continued

Side Chains attached to Free Amino Group at A, of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 265 | 4-ACETAMIDO BENZOIC ACID | 1 | 1 | 2 | 2 | 1 |
| 266 | 4-ACETOXY BENZOIC ACID | 1 | 2 | 2 | 2 | 1 |
| 267 | 4-ACETYL BENZOIC ACID | 2 | 2 | 4 | 1 | 1 |
| 268 | 4-AMINO BENZOIC ACID | 1 | 1 | 1 | 2 | 1 |

TABLE I-continued
Side Chains attached to Free Amino Group at A₂ of des-leucyl-p-chlorobiphenyl vancomycin and Biological Screening Results
| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 269 | 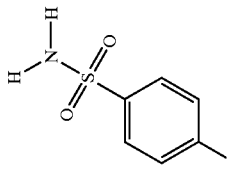 | 4-CARBOXY BENZENE SULFONAMIDE | 1 | 2 | 2 | 2 | 1 |
| 270 | 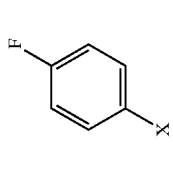 | 4-FLUORO BENZOIC ACID | 1 | 2 | 2 | 2 | 1 |
| 271 | 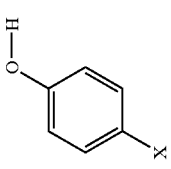 | 4-HYDROXY BENZOIC ACID | 1 | 2 | 2 | 4 | 1 |
| 272 | 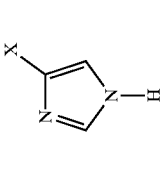 | 4-IMIDAZOLE CARBOXYLIC ACID | 1 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 273 | 4-METHOXY CINNAMIC ACID | 1 | 2 | 3 | 3 | 1 |
| 274 | 4-AMINO SALICYLIC ACID | 1 | 2 | 2 | 2 | 1 |
| 275 | 5-METHYL ISOXAZOLE-4-CARBOXYLIC ACID | 1 | 2 | 2 | 2 | 1 |
| 276 | 6-HYDROXY NICOTINIC ACID | 1 | 2 | 3 | 1 | 1 |

TABLE I-continued

Side Chains attached to Free Amino Group at A, of des-leucyl-p-chlorobiphenyl vancomycin and Biological Screening Results

| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 277 | | 6-HYDROXY PICOLINIC ACID | 1 | 2 | 3 | 2 | 1 |
| 278 | | 6-OXOHEPTANOIC ACID | 1 | 1 | 2 | 2 | 1 |
| 279 | | ACETIC ACID | 1 | 2 | 3 | 2 | 1 |
| 280 | | ANTHRANILIC ACID | 1 | 2 | 3 | 2 | 1 |
| 281 | | BENZOTRIAZOLE-5-CARBOXYLIC ACID | 1 | 2 | 2 | 2 | 1 |
| 282 | | COUMALIC ACID | 1 | 1 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 283 | PYRAZINE-2,3-DICARBOXYLIC ACID MONOAMIDE | 1 | 2 | 2 | 4 | 1 |
| 284 | D-DESTHIO BIOTIN | 1 | 2 | 3 | 2 | 1 |
| 285 | DIFLUOROACETIC ACID | 1 | 2 | 2 | 2 | 1 |
| 286 | DL-2-HYDROXY-N-BUTYRIC ACID | 1 | 2 | 2 | 2 | 1 |
| 287 | ETHOXYACETIC ACID | 1 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | Structure | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 288 | | FUMARIC ACID MONETHYL ESTER | 1 | 2 | 4 | 2 | 1 |
| 289 | | GLYOXYLIC ACID SEMICARBAZONE | 1 | 2 | 2 | 1 | 1 |
| 290 | | HEPTAFLUORO BUTYRIC ACID | 1 | 2 | 2 | 2 | 1 |
| 291 | | INDOLE-2-CARBOXYLIC ACID | 1 | 2 | 2 | 2 | 1 |
| 292 | | ISONICOTINIC ACID | 1 | 2 | 4 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 293 | ITACONIC ACID MONOMETHYL ESTER | 1 | 2 | 2 | 2 | 1 |
| 294 | LACTIC ACID | 1 | 2 | 3 | 2 | 1 |
| 295 | LEVULINIC ACID | 1 | 2 | 4 | 2 | 1 |
| 296 | MALEIC ACID MONOETHYL ESTER | 1 | 2 | 3 | 2 | 1 |
| 297 | MALEIC ACID MONOETHYL ESTER | 1 | 1 | 2 | 2 | 1 |
| 298 | 2,3-DIHYDRO-3-OXOPYRIDAZINE-6-CARBOXYLIC ACID | 1 | 1 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 299 | MAYBRIDGE BTB 09316 | | 1 | 1 | 2 | 4 | 1 |
| 300 | MAYBRIDGE KM 01502 | | 1 | 2 | 3 | 2 | 1 |
| 301 | MAYBRIDGE KM 06000 | | 1 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 302 | 3-(4-CHLORO BENZENE SULPHONYL) BUTYRIC ACID | 1 | 3 | 4 | 3 | 1 |
| 303 | METHOXYACETIC ACID | 1 | 2 | 4 | 4 | 1 |
| 304 | MONO-MEHTYL GLUTARATE | 1 | 2 | 4 | 3 | 1 |
| 305 | MOMO-METHYL SUCCINATE | 1 | 2 | 4 | 3 | 1 |
| 306 | N-[3-(2-FURYL ACRYLOYL)]-GLYCINE | 1 | 2 | 3 | 2 | 1 |
| 307 | NICOTINIC ACID | 1 | 3 | 4 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 308 | NICOTINIC ACID N-OXIDE | | 1 | 2 | 4 | 2 | 1 |
| 309 | N-METHYL MALEAMIC ACID | | 1 | 2 | 3 | 2 | 1 |
| 310 | PENTAFLUORO PHENYLACETIC ACID | | 1 | 2 | 4 | 2 | 1 |
| 311 | PERFLUORO PENTANOIC ACID | | 1 | 1 | 2 | 1 | 1 |
| 312 | PICOLINIC ACID | | 1 | 2 | 2 | 2 | 1 |
| 313 | PICOLINIC ACID N-OXIDE | | 1 | 2 | 2 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | Structure | E. faecium ATCC 49624 | S. epidermidis ATCC 12228 | S. aureus ATCC 29213 | E. faecalis CL 4877 | E. faecalis ATCC 29212 |
|---|---|---|---|---|---|---|---|
| 314 | PYRUVIC ACID | | 1 | 2 | 2 | 2 | 1 |
| 315 | SALICYLIC ACID | | 1 | 1 | 1 | 2 | 1 |
| 316 | TETRAHYDRO-2-FUROIC ACID | | 1 | 2 | 2 | 3 | 1 |
| 317 | TETRAHYDRO-3-FUROIC ACID | | 1 | 3 | 4 | 2 | 1 |
| 318 | THIOPHENE-2-ACETIC ACID | | 1 | 2 | 4 | 3 | 1 |
| 319 | THIOPHENE-2-CARBOXYLIC ACID | | 1 | 2 | 3 | 2 | 1 |
| 320 | THIOPHENE-3-ACETIC ACID | | 1 | 2 | 3 | 2 | 1 |

TABLE I-continued

Side Chains attached to Free Amino Group at A₂ of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 321 | UROCANIC ACID | 1 | 2 | 2 | 2 | 1 |
| 322 | HSE(ME) | 1 | 2 | 2 | 2 | 1 |
| 323 | L-THREONINE MONOHYDRATE | 1 | 2 | 2 | 2 | 1 |
| 324 | N-ACETYL-DL-HISTIDINE HYDRATE | 1 | 2 | 2 | 2 | 1 |

TABLE I-continued

Side Chains attached to Free Amino Group at A, of des-leucyl-p-chlorobiphenyl vancomycin and Biological Screening Results

| Cmpd No. | Reagent Name | E. faecium ATCC 49624 | S. epidermidis ATCC 12228 | S. aureus ATCC 29213 | E. faecalis CL 4877 | E. faecalis ATCC 29212 |
|---|---|---|---|---|---|---|
| 325 | N-FORMYL-DL-ALANINE | 1 | 2 | 3 | 2 | 1 |
| 326 | N-FORMYL-DL-METHIONINE | 1 | 2 | 2 | 2 | 1 |
| 327 | OXAMIC ACID | 1 | 2 | 3 | 3 | 1 |

In Table II, below, MIC (minimum inhibitory concentration) values of certain compounds of the present invention are provided for the bacterial strains E. faecium ATCC 49624, E. faecium CL 4931, E. faecalis ATCC 29212, E. Faecalis CL 4877, S aureus ATCC 29213, and S. Aureus ATCC 33591. The minimum inhibitory concentrations (MIC) of test compounds were determined using bacteria grown in brain heart infusion media (BHI) supplemented with 0.1% casamino acids. Logarithmically growing cells were diluted to approximately $5 \times 10^5$ CFU/ml and subjected to test compounds solubilized and serially diluted in DMSO. A 5% final DMSO concentration had no affect on cell viability or killing. After 18 hours at 37° C., the $OD_{600}$ was determined by reading the ninety-six well microtiter plates on a microplate reader. For a given concentration, an MIC determination was made if:

$$[OD_{600}\text{Control} - OD_{600}\text{Test Conc.}]/[OD_{600}\text{Control} - OD_{600}\text{Media}] \times 100 \geq 90\%$$

TABLE II

MIC Values of Compounds of the Invention Against Selected Baterial Strains

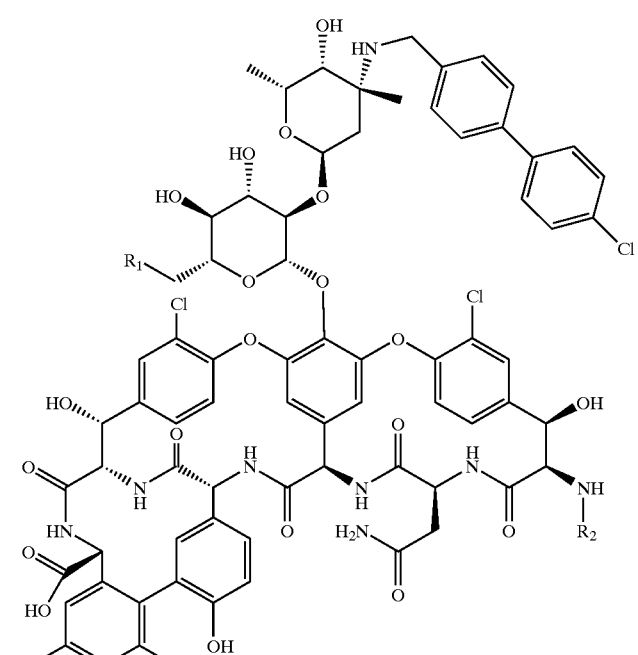

| Cmpd No. | R1 | R2 | Reagent Name | E. faecium ATCC 49624 | E. faecium CL 4931 | E. faecalis ATCC 29212 | E. faecalis CL 4877 | S. aureus ATCC 29213 | S. aureus ATCC 33591 |
|---|---|---|---|---|---|---|---|---|---|
| 0 | OH | 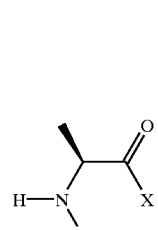 | Vancomycin (Vancosamine sugar is unsubstituted in this compound only.) | 1.25 | >250 | 3.12 | >250 | 1.25 | 2.5 |
| 1 | OH | | L-ALA | 0.78 | 25 | 1.56 | 25 | 0.78 | 0.78 |

TABLE II-continued

*MIC Values of Compounds of the Invention Against Selected Baterial Strains*

| | | | | | | | | | |
|---|---|---|---|---|---|---|---|---|---|
| 7 | OH | (L-Phe side chain structure) | L-PHE | 0.12 | 6.25 | 0.78 | 6.25 | 0.39 | 0.39 |
| 11 | OH | (L-Thr(Trt) side chain structure) | L-THR(TRT) | 3.12 | 6.25 | 3.12 | 3.12 | 3.12 | 3.12 |
| 12 | OH | (L-Trp side chain structure) | L-TRP | 0.39 | 6.25 | 1.56 | 3.12 | 0.78 | 0.78 |
| 15 | OH | (D-Met side chain structure) | D-MET | 0.12 | 12.5 | 0.25 | 12.5 | 0.25 | 0.12 |
| 16 | OH | (D-Phe side chain structure) | D-PHE | 0.12 | 12.5 | 0.25 | 12.5 | 0.25 | 0.25 |
| 17 | OH | (D-Ser(tBu) side chain structure) | D-SER(TBU) | 0.062 | 6.25 | 0.25 | 3.91 | 0.062 | 0.12 |

TABLE II-continued

MIC Values of Compounds of the Invention Against Selected Baterial Strains

| 18 | OH | (structure) | D-THR(TBU) | 0.25 | 25 | 1.56 | 25 | 0.78 | 0.78 |
| --- | --- | --- | --- | --- | --- | --- | --- | --- | --- |
| 20 | OH | (structure) | L-VAL | 0.25 | 12.5 | 0.78 | 3.12 | 0.25 | 0.39 |
| 21 | OH | (structure) | L-(+)-LACTIC ACID | 3.12 | 25 | 6.25 | 25 | 1.56 | 3.12 |
| 24 | OH | (structure) | PIPEPAZIN-1-YL ACETIC ACID HYDRATE | 1.56 | 25 | 1.56 | 6.25 | 0.78 | 0.78 |
| 25 | OH | (structure) | D-TRP | 0.25 | 12.5 | 0.39 | 6.25 | 0.25 | 0.25 |
| 26 | OH | (structure) | L-GLU(OBZL) | 1.56 | >25 | 1.56 | 12.5 | 0.78 | 0.78 |
| 30 | OH | (structure) | L-HYP(TBU) | 0.78 | 25 | 3.12 | 25 | 1.56 | 1.56 |

TABLE II-continued
MIC Values of Compounds of the Invention Against Selected Baterial Strains
| | | | | | | | | | |
|---|---|---|---|---|---|---|---|---|---|
| 34 | OH | 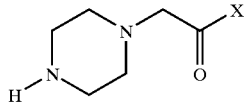 | 4-CARBOXY METHYL- PIPERAZINE | 0.78 | 25 | 3.12 | 6.25 | 0.78 | 1.56 |
| 36 | OH | 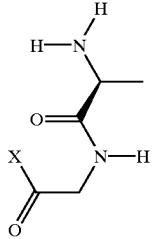 | L-ALA-GLY | 0.12 | 12.5 | 0.78 | 6.25 | 0.39 | 0.39 |
| 37 | OH | 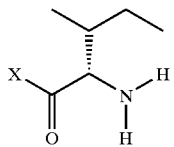 | L-ILE | 0.25 | 12.5 | 0.78 | 3.12 | 0.39 | 0.39 |
| 38 | OH | 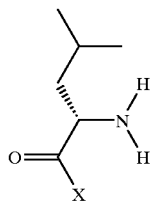 | L-LEU | 0.78 | 12.5 | 1.56 | 12.5 | 0.78 | 0.78 |
| 41 | OH | 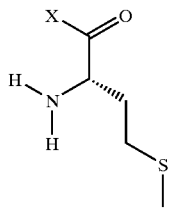 | L-MET | 0.25 | 12.5 | 0.78 | 12.5 | 0.39 | 0.39 |
| 42 | OH | 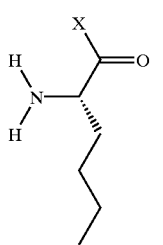 | L-NLE | 0.39 | 12.5 | 0.78 | 6.25 | 0.39 | 0.39 |
| 56 | OH | 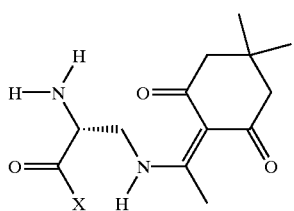 | D-DPR(DDE) | 0.12 | 12.5 | 0.78 | 12.5 | 0.25 | 0.25 |

TABLE II-continued

*MIC Values of Compounds of the Invention Against Selected Baterial Strains*

| 56-3 | OH [structure] | D-DPR(DDE) Deprotect/Rearrange | 0.12 | 6.25 | 0.25 | 6.25 | 0.25 | 0.25 |
|---|---|---|---|---|---|---|---|---|
| 61 | OH [structure] | D-LYS (CARBAMYL) | 0.12 | 12.5 | 0.25 | 12.5 | 0.12 | 0.12 |
| 62 | OH [structure] | D-ORN (CARBAMYL) | 0.12 | 12.5 | 0.25 | 12.5 | 0.25 | 0.25 |
| 63 | OH [structure] | D-SER | 0.78 | 25 | 1.56 | 12.5 | 0.78 | 0.78 |
| 64 | OH [structure] | D-THR | 0.39 | 25 | 1.56 | 12.5 | 0.78 | 0.78 |

TABLE II-continued

MIC Values of Compounds of the Invention Against Selected Baterial Strains

| # | R | Structure | Peptide | | | | | | |
|---|---|---|---|---|---|---|---|---|---|
| 67 | OH | | GLY-GLY-GLY | 0.78 | 12.5 | 1.56 | 6.25 | 0.78 | 0.78 |
| 68 | OH | | GLY-GLY | 0.39 | 12.5 | 1.56 | 6.25 | 0.78 | 0.78 |
| 75 | OH | | L-LYS(BIOTIN) | 0.39 | 25 | 3.12 | 25 | 1.56 | 1.56 |
| 79 | OH | | L-LYS(FOR) | 0.78 | 25 | 3.12 | 25 | 1.56 | 1.56 |
| 81 | OH | | L-MET(O) | 0.78 | 25 | 1.56 | 25 | 0.78 | 1.56 |

TABLE II-continued

*MIC Values of Compounds of the Invention Against Selected Bacterial Strains*

| # | | Structure | Name | | | | | |
|---|---|---|---|---|---|---|---|---|
| 82 | OH | (structure) | L-MET(O2) | 0.39 | 25 | 1.56 | 12.5 | 0.78 | 0.78 |
| 83 | OH | (structure) | L-ORN(PYRAZINYL CARBONYL) | 0.25 | 25 | 0.78 | 12.5 | 0.39 | 0.78 |
| 88 | OH | (structure) | L-SER | 0.78 | 12.5 | 1.56 | 25 | 0.78 | 1.56 |
| 89 | OH | (structure) | L-THR | 0.78 | >25 | 3.12 | 12.5 | 1.56 | 1.56 |
| 91 | OH | (structure) | N-ALPHA-L-GLUTAMINE | 0.78 | 25 | 1.56 | 12.5 | 0.78 | 0.78 |
| 100 | OH | (structure) | 2-(2-METHOXY ETHOXY) ACETIC ACID | 0.78 | 6.25 | 1.56 | 6.25 | 0.25 | 0.78 |

TABLE II-continued

MIC Values of Compounds of the Invention Against Selected Baterial Strains

| 108 | OH | [structure] | 4-NITROBENZOYL-GLYCYL-GLYCINE | 1.56 | >25 | 3.12 | >25 | 0.78 | 0.78 |
| --- | --- | --- | --- | --- | --- | --- | --- | --- | --- |
| 135 | OH | [structure] | BOC-D-ASN | 0.39 | >25 | 3.12 | 12.5 | 1.56 | 1.56 |
| 136 | OH | [structure] | BOC-D-GLN | 0.78 | >25 | 1.56 | 12.5 | 0.78 | 0.78 |
| 188 | OH | [structure] | N-ALPHA-CARBOETHOXY-L-ASPARAGINE | 0.062 | 6.25 | 0.39 | 3.12 | 0.39 | 0.39 |
| 257 | OH | [structure] | 3-AMINOBENZOIC ACID | 0.39 | 25 | 1.56 | 12.5 | 0.78 | 0.78 |
| 287 | OH | [structure] | ETHOXYACETIC ACID | 1.56 | 25 | 3.12 | 12.5 | 1.56 | 3.12 |

TABLE II-continued

MIC Values of Compounds of the Invention Against Selected Baterial Strains

| | | | | | | | | | |
|---|---|---|---|---|---|---|---|---|---|
| 303 | OH | | METHOXYACETIC ACID | 1.56 | 25 | 3.12 | 12.5 | 1.56 | 1.56 |
| 328 | OH | | D-ME-VAL | 0.12 | 12.5 | 0.39 | 12.5 | 0.25 | 0.25 |
| 329 | OH | | D-ME-LEU | 0.031 | 6.25 | 0.12 | 6.25 | 0.25 | 0.12 |
| 330 | OH | | L-ME-ILE | 0.12 | 12.5 | 0.78 | 3.12 | 0.25 | 0.25 |
| 331 | OH | | L-ME-SER(BZL) | 0.39 | 12.5 | 1.56 | 6.25 | 0.78 | 0.78 |
| 332 | OH | | L-CYS(BZL) | 1.56 | 25 | 3.12 | 12.5 | 1.56 | 1.56 |
| 333 | OH | | L-CYS(TBU) | 1.56 | 25 | 3.12 | 25 | 1.56 | 1.56 |

TABLE II-continued

MIC Values of Compounds of the Invention Against Selected Baterial Strains

| | | | | | | | | | |
|---|---|---|---|---|---|---|---|---|---|
| 334 | OH | [structure] | D-CYS(TBU) | 0.12 | 25 | 0.78 | 12.5 | 0.25 | 0.25 |
| 335 | OH | [structure] | D-ILE | 0.12 | 12.5 | 0.39 | 12.5 | 0.12 | 0.25 |
| 336 | OH | [structure] | D-LEU | 0.12 | 6.25 | 0.25 | 12.5 | 0.25 | 0.25 |
| 337 | OH | [structure] | D-NVA | 0.062 | 12.5 | 0.25 | 12.5 | 0.12 | 0.12 |
| 338 | OH | [structure] | D-SER(BZL) | 0.25 | 12.5 | 1.56 | 25 | 1.56 | 0.39 |
| 339 | OH | [structure] | D-VAL | 0.12 | 12.5 | 0.25 | 12.5 | 0.25 | 0.25 |
| 340 | OH | [structure] | L-ME-VAL | 0.39 | 12.5 | 1.56 | 25 | 0.39 | 0.39 |

TABLE II-continued

MIC Values of Compounds of the Invention Against Selected Baterial Strains

| # | | Structure | Name | | | | | | |
|---|---|---|---|---|---|---|---|---|---|
| 341 | OH | (structure) | L-NVA | 0.78 | 12.5 | 1.56 | 25 | 0.78 | 0.78 |
| 342 | OH | (structure) | L-SER(BZL) | 0.39 | 25 | 1.56 | 12.5 | 0.78 | 0.78 |
| 343 | OH | (structure) | L-SER(TBU) | 0.39 | 25 | 3.12 | 12.5 | 1.56 | 0.78 |
| 344 | OH | (structure) | L-THR(TBU) | 0.78 | 25 | 3.12 | 12.5 | 1.56 | 1.56 |
| 345 | OH | (structure) | L-CYS(STBU) | 0.39 | 25 | 3.12 | 12.5 | 0.78 | 0.78 |
| 517 | OH | (structure) | TS0517 (Cl-Biphenyl Vancomycin) | 0.062 | 12.5 | 0.25 | 12.5 | 0.25 | 0.25 |
| 518 | OH | X—H | TS0518(Des-Lecyl Cl-Biphenyl Vanc) | 1.56 | 12.5 | 3.12 | 25 | 3.12 | 6.25 |

TABLE II-continued

MIC Values of Compounds of the Invention Against Selected Baterial Strains

| 519 | I | [structure] | 6'-Deoxy-6'-Iodo | 0.78 | >25 | 3.12 | >25 | 1.56 | 3.12 |
| --- | --- | --- | --- | --- | --- | --- | --- | --- | --- |
| 520 | I | [structure] | 6'-Deoxy-6'-Iodo-ChloroBiphenyl | 0.12 | 12.5 | 0.78 | 12.5 | 0.78 | 0.78 |
| 521 | $NH_2$ | [structure] | 6'-Deoxy-6'-Amino TS1017 | 0.12 | 12.5 | 0.78 | 6.25 | 0.78 | 0.78 |
| 522 | OH | X—H | Des-Lecyl Vancomycin | >25 | >25 | >25 | >25 | >25 | >25 |
| 523 | $NH_2$ | [structure] | 6'-Deoxy-6'-Amino TS0517 | 0.12 | 6.25 | 0.25 | 6.25 | 0.78 | 0.39 |
| 524 | OH | [structure] | D-SER(ET) | 0.25 | 25 | 1.56 | 12.5 | 0.39 | 0.39 |
| 525 | OH | [structure] | D-SER(ME) | 0.25 | 25 | 1.56 | 25 | 0.39 | 0.39 |
| 526 | OH | [structure] | N-Methyl-L-SER(TBU) | 0.25 | 25 | 0.78 | 6.25 | 0.39 | 0.39 |

TABLE II-continued

MIC Values of Compounds of the Invention Against Selected Baterial Strains

| 527 | OH | [structure] | N-Methyl-D-SER(ET) | 0.25 | 25 | 1.56 | 12.5 | 0.39 | 0.39 |
| --- | --- | --- | --- | --- | --- | --- | --- | --- | --- |
| 528 | OH | [structure] | D-SER(ISOPROPYL) | 0.12 | 25 | 0.78 | 12.5 | 0.25 | 0.25 |
| 529 | OH | [structure] | L-SER(ISOPROPYL) | 0.12 | 25 | 0.78 | 12.5 | 0.25 | 0.25 |
| 554 | OH | [structure] | L-HIS | 0.39 | 12.5 | 3.12 | 25 | 1.56 | 0.78 |
| 555 | OH | [structure] | D-HIS | 0.39 | 12.5 | 1.56 | 12.5 | 0.78 | 0.39 |
| 556 | OH | [structure] | D-GLY-(2-Pyridyl) | 0.39 | 25 | 0.78 | 25 | 0.78 | 0.39 |

TABLE II-continued

MIC Values of Compounds of the Invention Against Selected Baterial Strains

| 557 | OH (structure) | L-Phe-(3-Nitro-2-Hydroxy) | 0.39 | 25 | 1.56 | 25 | 1.56 | 1.56 |
|---|---|---|---|---|---|---|---|---|

What is claimed is:

1. A compound having the formula $A_1$-$A_2$-$A_3$-$A_4$-$A_5$-$A_6$-$A_7$ wherein each of the groups $A_2$ to $A_7$ comprises a modified or unmodified α-amino acid residue, $A_1$ is optional and, when present, comprises an organic group-other than N-substituted leucine, and at least one of the groups $A_1$ to $A_7$ is linked via a glycosidic bond to one or more glycosidic groups each having one or more sugar residues, wherein at least one of said one or more glycosidic groups comprises a glucose residue with the $C_6$ position of said glucose residue modified to bear at least one substituent other than hydroxyl, and wherein at least one of said sugar residues is modified to bear at least one hydrophobic substituent.

2. The compound of claim 1 wherein at least one of said one or more glycosidic groups is a disaccharide modified to bear said at least one hydrophobic substituent.

3. The compound of claim 1 wherein each of the groups $A_2$, $A_4$, $A_5$, $A_6$ and $A_7$ bears an aromatic side chain and the aromatic side chains of groups $A_2$ and $A_6$ are linked to the aromatic side chain of group $A_4$ via ether linkages and the aromatic side chains of groups $A_5$ and $A_7$ are linked to each other via a carbon-carbon bond.

4. The compound of claim 3 wherein the group $A_4$ is linked to a glycosidic group modified to bear said at least one hydrophobic substituent.

5. The compound of claim 4 wherein at least one of said one or more glycosidic groups is a disaccharide comprising a glucose residue directly bonded to group $A_4$ and a vancosamine residue bonded to said glucose residue.

6. The compound of claim 5 wherein $A_2$-$A_3$-$A_4$-$A_5$-$A_6$-$A_7$ is as found in a compound selected from the group consisting of vancomycin, eremomycin, chloroeremomycin, and β-avoparcin.

7. The compound of claim 6 wherein $A_2$-$A_3$-$A_4$-$A_5$-$A_6$-$A_7$ is as found in vancomycin.

8. The compound of claim 1 wherein said at least one substituent other than hydroxyl is a polar substituent.

9. The compound of claim 1 wherein said at least one substituent other than hydroxyl is a hydrophobic substituent.

10. The compound of claim 7 wherein the vancosamine residue in vancomycin is N-substituted with said at least one hydrophobic substituent.

11. The compound of claim 7 wherein said glucose residue directly bonded to group $A_4$ is modified to bear at least one substituent other than hydroxyl and said vancosamine residue is N-substituted with said at least one hydrophobic substituent.

12. The compound of claim 11 wherein said at least one substituent other than hydroxyl is a polar substituent.

13. The compound of claim 1 wherein said at least one hydrophobic substituent is R, OR, $NR_1R$, SR, $SO_2R$, C(O)OR, C(O)SR, C(S)OR, C(S)SR, $NR_1C(O)R$, $C(O)NR_1R$, or their halogen substituted derivatives and R is alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl; $R_1$ is hydrogen, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl; and any pharmaceutically acceptable salts thereof; and when two or more of said substituents are present, they are the same or different.

14. The compound of claim 1 wherein said organic group is selected from the group consisting of a modified or unmodified alpha amino acid residue, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl, arylsulfonyl, guanidinyl, carbamoyl, and xanthyl.

15. The compound of claim 1 wherein the group $A_7$ bears a terminal carboxyl, ester, thioester, amide, N-substituted amide, or other carboxylic acid derivative.

16. A method for making a compound of the formula $A_1-A_2-A_3-A_4-A_5-A_6-A_7$ wherein each of the groups $A_2$ to $A_7$ comprises a modified or unmodified α-amino acid residue, $A_1$ comprises an organic group other than N-substituted leucine, and at least one of the groups $A_1$ to $A_7$ is linked via a glycosidic bond to one or more glycosidic groups each having one or more sugar residues, wherein at least one of said one or more glycosidic groups comprises a glucose residue with the $C_6$ position of said glucose residue modified to bear at least one substituent other than hydroxyl, and wherein at least one of said sugar residues is modified to bear at least one hydrophobic substituent, said method comprising removing the N-substituted leucine residue from the compound N-substituted-leucyl-$A_2-A_3-A_4-A_5-A_6-A_7$ thereby forming a compound having a free amino group at $A_2$; and attaching an organic group $A_1$ to the free amino group at $A_2$.

17. The method of claim 16 wherein the N-substituted leucine residue is N-methyl leucine.

18. The method of claim 16 wherein at least one of said one or more glycosidic groups is a disaccharide modified to bear said at least one hydrophobic substituent.

19. The method of claim 16 wherein each of the groups $A_2, A_4, A_5, A_6$ and $A_7$ bears an aromatic side chain and the aromatic side chains of groups $A_2$ and $A_6$ are linked to the aromatic side chain of group $A_4$ via ether linkages and the aromatic side chains of groups $A_5$ and $A_7$ are linked to each other via a carbon-carbon bond.

20. The method of claim 19 wherein the group $A_4$ is linked to a glycosidic group having one or more sugar residues modified to bear said at least one hydrophobic substituent.

21. The method of claim 20 wherein said glycosidic group is a disaccharide comprising a glucose residue directly bonded to group $A_4$ and a vancosamine residue bonded to said glucose residue.

22. The method of claim 21 wherein $A_2-A_3-A_4-A_5-A_6-A_7$ is as found in a compound selected from the group consisting of vancomycin, eremomycin, chloroeremomycin, and β-avoparcin.

23. The method of claim 22 wherein $A_2-A_3-A_4-A_5-A_6-A_7$ is as found in vancomycin.

24. The method of claim 16 wherein said at least one substituent other than hydroxyl is a polar substituent.

25. The compound of claim 16 wherein said at least one substituent other than hydroxyl is a hydrophobic substitutent.

26. The method of claim 23 wherein the vancosamine residue in vancomycin is N-substituted with said least one hydrophobic substituent.

27. The method of claim 23 wherein said glucose residue directly bonded to group $A_4$ is modified to bear at least one substituent other than hydroxyl and said vancosamine residue is N-substituted with said least one hydrophobic substituent.

28. The method of claim 27 wherein said substituent other than hydroxyl is a polar substituent.

29. The method of claim 16 wherein said at least one hydrophobic substituent is R, OR, $NR_1R$, SR, $SO_2R$, C(O)OR, C(O)SR, C(S)OR, C(S,)SR, $NR_1C(O)R$, $C(O)NR_1R$, or their halogen substituted derivatives and R is alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl; $R_1$ is hydrogen, alkyl, aryl, aralkyl, alkanoyl, aroyl, aralkanoyl, heterocyclic, heterocyclic-carbonyl, heterocyclic-alkyl, heterocyclic-alkyl-carbonyl; alkylsulfonyl or arylsulfonyl; and any pharmaceutically acceptable salts thereof; and when two or more of said substituents are present, they are the same or different.

30. The method of claim 16 wherein said organic group is selected from the group consisting of a modified or unmodified alpha amino acid residue, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl, arylsulfonyl, guanidinyl, carbamoyl, and xanthyl.

31. The method of claim 16 wherein the group $A_7$ bears a terminal carboxyl, ester, thioester, amide, N-substituted amide, or other carboxylic acid derivative.

32. A method for making a glycopeptide antibiotic having the formula $A_1-A_2-A_3-A_4-A_5-A_6-A_7$ wherein $A_2-A_3-A_4-A_5-A_6-A_7$ is as found in vancomycin and $A_1$ comprises an organic group other than N-substituted leucine, said method comprising modifying vancomycin to form a first modified vancomycin bearing a substituent other than hydroxyl at the $C_6$ position of the glucose attached to $A_4$ of vancomycin;

modifying said first modified vancomycin to form a second modified vancomycin bearing a hydrophobic substituent at the vancosamine nitrogen;

removing the N-methyl leucine residue from said second modified vancomycin to form a des-N-methyl leucyl second modified vancomycin bearing a free amino group at $A_2$; and, attaching an organic group $A_1$ to the amino group at $A_2$.

33. The method of claim 32 wherein said substituent other than hydroxyl is a polar substituent.

34. The method of claim 32 wherein said organic group is selected from the group consisting of a modified or unmodified alpha amino acid residue, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl, arylsulfonyl, guanidinyl, carbamoyl, and xanthyl.

35. A method of treating a gram-positive bacterial infection in a host comprising administering to said host an effective amount of a compound of claim 1 or a pharmaceutically acceptable salt or ester thereof.

36. The method of claim 35 wherein the host is a mammal.

37. The method of claim 36 where the mammal is a human.

38. The method of claim 35 further comprising administering to said host one or more additional drugs or therapeutic agents in combination with a compound of claim 1 or a pharmaceutically acceptable salt or ester thereof.

39. A composition comprising a compound of claim 1 or a pharmaceutically acceptable salt or ester thereof and a pharmaceutically acceptable carrier or excipient.

40. The composition of claim 39 further comprising one or more additional drugs or therapeutic agents.

* * * * *